US006337316B1

(12) United States Patent
El Tayar et al.

(10) Patent No.: US 6,337,316 B1
(45) Date of Patent: Jan. 8, 2002

(54) PHARMACEUTICAL COMPOSITIONS THEREOF, AND METHODS OF USING SAME

(75) Inventors: Nabil El Tayar, Milton; Steven Blechner, West Bridgewater; Brad Jameson, Milton; Mark Tepper, Canton, all of MA (US)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

(21) Appl. No.: 09/460,384

(22) Filed: Dec. 13, 1999

Related U.S. Application Data

(63) Continuation of application No. PCT/US98/12312, filed on Jun. 11, 1998.
(60) Provisional application No. 60/049,470, filed on Jun. 12, 1997.

(51) Int. Cl.$^7$ ......................... A61K 38/10; A61K 38/12; C07K 7/00; C07K 7/64

(52) U.S. Cl. ...................... 514/9; 514/1; 514/2; 514/14; 514/15; 530/317; 530/321; 530/326; 530/327

(58) Field of Search ............................... 530/317, 321, 530/326, 327; 514/1, 2, 9, 14, 15, 885; 424/184.1, 185.1

(56) References Cited

U.S. PATENT DOCUMENTS 5,192,746 A    3/1993   Lobl et al.
5,888,763 A  * 3/1999   Hanafusa et al.

FOREIGN PATENT DOCUMENTS

EP           0757099       2/1997
WO           93/00431      1/1993
WO           WO 96/31229  10/1996

OTHER PUBLICATIONS

Arima et al., "Inhibition by CTLA4Ig of Experimental Allergic Encephalomyelitis", The Journal of Immunology, vol. 156, pp. 4916–4924, (1996).
Aruffo et al., Molecule cloning of a CD28 cDNA by a high–efficiency COS cell expression system, Proc. Natl. Acad. Sci., vol. 84, pp. 8573–8577, (1987).
Azuma et al., "B70 antigen is a second ligand for CTLA–4 and CD28", Letters to Nature, vol. 366, pp. 76–79, (1993).
Boussiotis et al., B7 But Not Intercellular Adhesion Molecule–1 Costimulation Prevents the Induction of Human Alloantigen–specific Tolerance, J. Exp. Med., vol. 178, pp. 1753–1763, (1993).
Chu et al., "Intervention of CD4+ Cell Subset Shifts and Autoimmunity in the BXSB Mouse by Murine CTLA4Ig", The Journal of Immunology, vol. 156, pp. 1262–1268, (1996).

Cross et al., "Long–Term Inhibition of Murine Experimental Autoimmune Encephalomyelitis Using CTLA–4–Fc Supports a Key Role for CD28 Costimulation", J. Clin. Invest., vol. 95, pp. 2783–2789, (1995).
Ellis et al., "Interatctions of CD80 and CD86 with CD28 and CTLA4", The Journal of Immunology, vol. 156, pp. 2700–2709, (1996).
Finck et al., "Treatment of Murine Lupus with CTLA4Ig", Science, vol. 265, pp. 1225–1227, (1994).
Freeman et al., "CTLA–4 and CD28 mRNA are Coexpressed in Most T Dells After Activation", The Journal of Immunology, vol. 149, No. 12, pp. 3795–2801, (1992).
Geppert, Phytohemagglutinin (PHA), pp. 1233–1234 in Encyclopedia of Immunology, (eds) Roitt, IM and Delves, PJ, Academic Press, London. 1992.
Guo ett al, "Mutational Analysis and Alternatively Spliced Product of B7 Defined Its CD28/CTLA4–binding Site on Immunoglobulin C–like Domain", J. Exp. Med., vol. 181, pp. 1345–1355, (1995).
Hathcock et al., "Comparative Analysis of B7–1 and B7–2 Costimulatory Ligands: Expression and Function", The Journal of Experimental Medicine, vol. 180, pp. 631–640, (1994).
Harding et al., "CD280mediated signaling co–stimulated murine T cells and prevents induction of anergy in T–cell clones", Nature, vol. 356, pp. 607–609, (1992).
Judge et al., "The In Vivo Mechanism of Action of CTLA4Ig", The Journal of Immunology, vol. 156, pp. 2294–2299. (1996).
Lenschow et al., "Long–Term Survival of Xenogeneic Pancreatic Islet Grafts Induced by CTLA4Ig", Science, vol. 257, pp. 789–792, (1992).
Lenschow et al., "Differential Effects of Anti–B7–1 and Anti–B7–2 Monoclonal Antibody Treatment on the Development of Diabetes in the Nonobese Diabetic Mouse", J. Exp. Med., vol. 181, pp. 1145–1155, (1995).
Lenschow et al., "CD28/B7 System of T Cell Constimulation", Annu. Rev. Immunol., vol. 14, pp. 233–258, (1996).
Hathcock et al., "Comparative Analysis of B7–1 and B7–2 Costimulatory Ligands: Expression and Function", The Journal of Experimental Medicine, vol. 180, pp. 631–640, (1994).

(List continued on next page.)

Primary Examiner—Phillip Gambel
Assistant Examiner—Jessica H. Roark
(74) Attorney, Agent, or Firm—Browdy and Neimark

(57) ABSTRACT

The present invention relates to peptidomimetics capable of inhibiting CD28 and/or CTLA-4 interaction with CD80 (B7-1) and CD86 (B7-2) and having a core amino acid sequence, LeuMetTyrProProProTyrTyr, corresponding to residues 2 to 9 of SEQ ID NO:1. The present invention also relates to pharmaceutical compositions and a method of treating pathologies and disorders which are improved by inhibition of CD28 and/or CTLA-4 interaction with CD80 and CD86.

6 Claims, 11 Drawing Sheets

OTHER PUBLICATIONS

Figure 1:
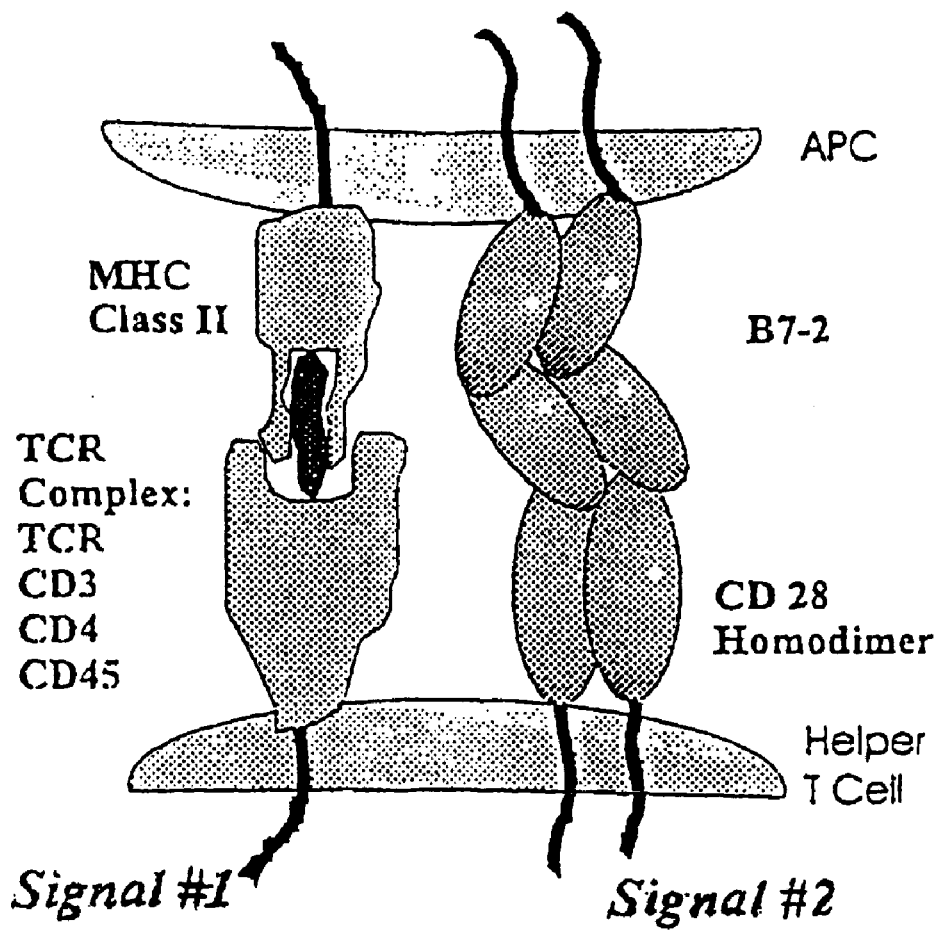
Figure 3:
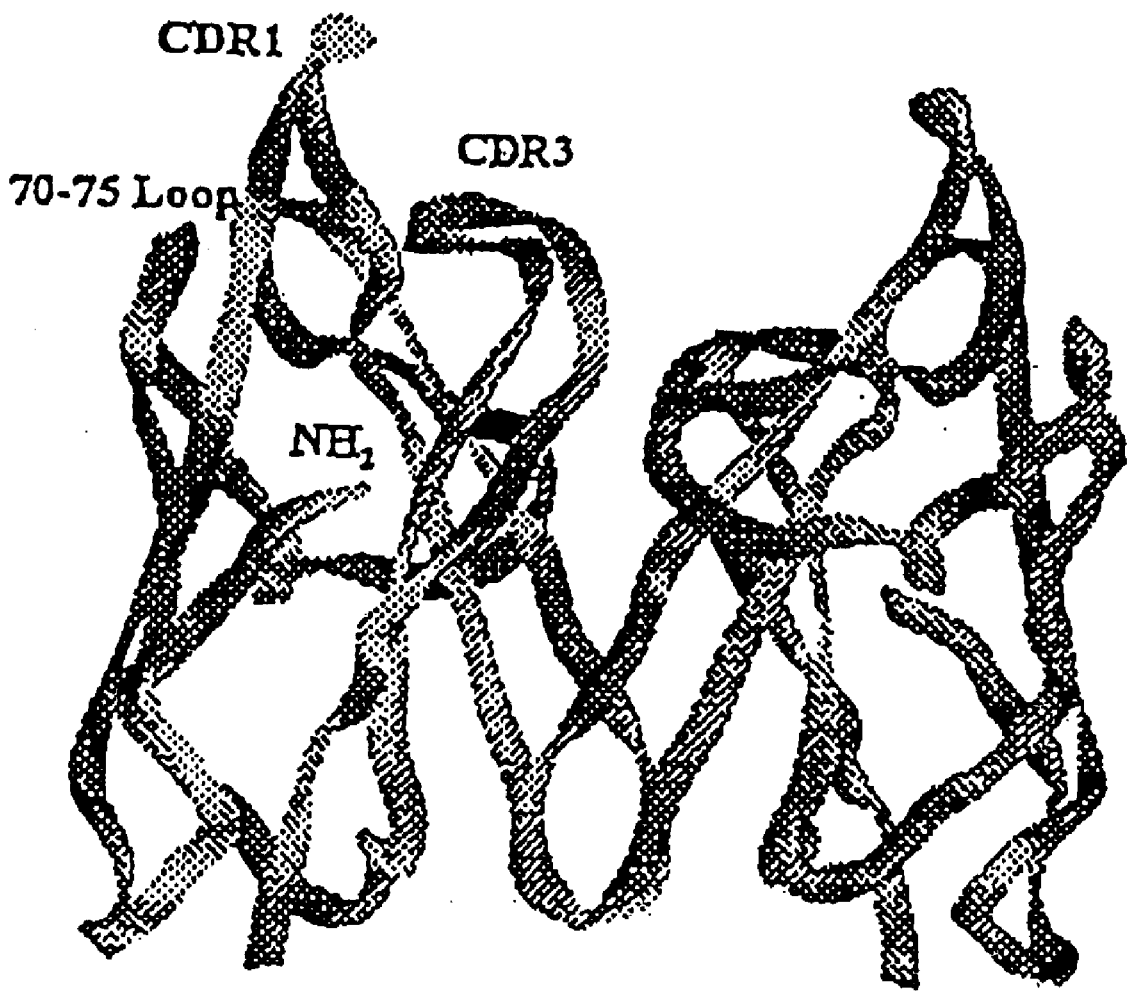
Figure 5:
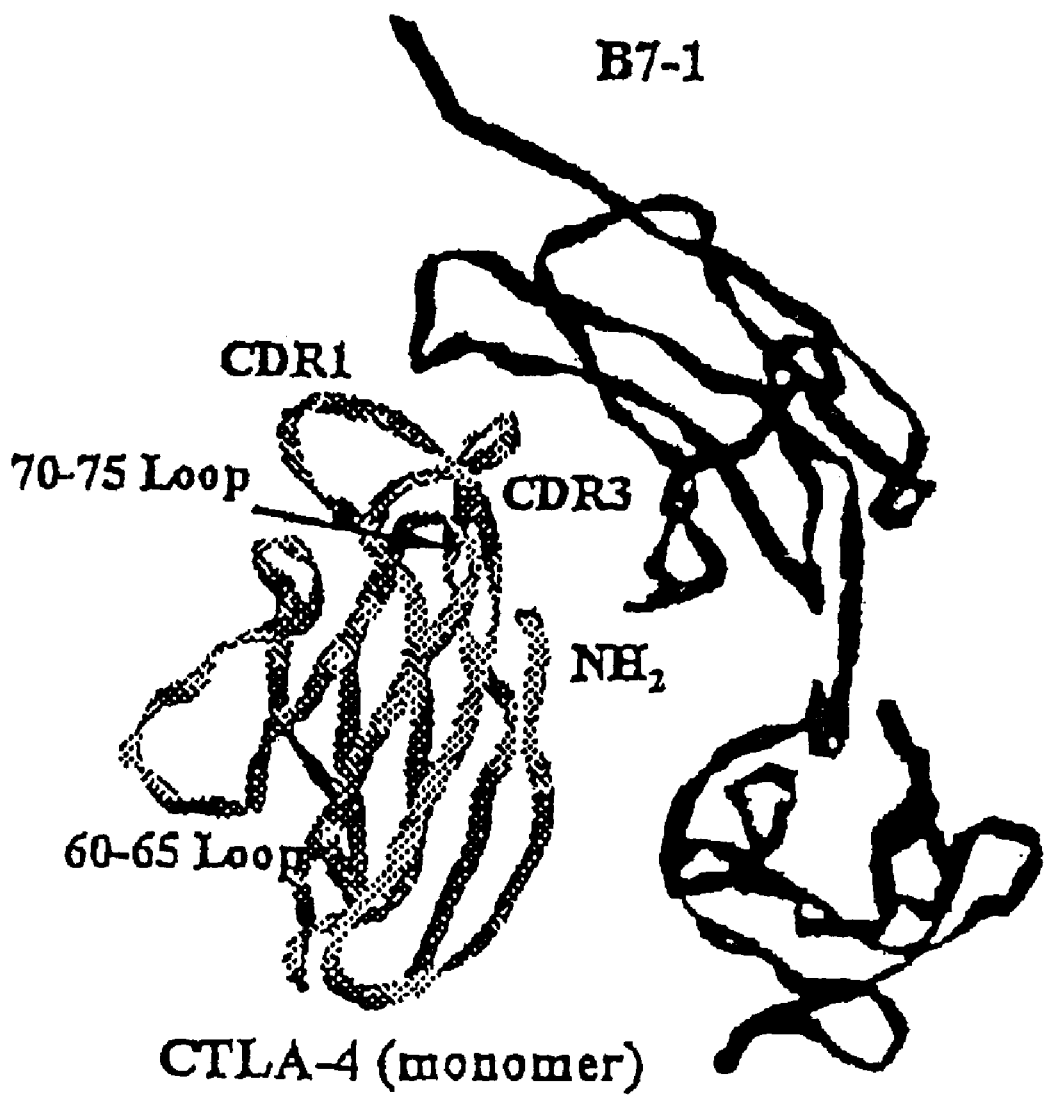

Lin et al., "Long–Term Acceptance of Major Histocompatibility Complex Mismatched Cardiac Allografts Induced by CTLA4Ig Plus Donor–specific Transfusion", *J. Exp. Med.*, vol. 178, pp. 1801–1806, (1993).

Linsley et al., "CTLA–4 Is a Second Receptor for the B Cell Activation Antigen B7", *J Exp. Med.*, vol. 174, pp. 561–569, (1991).

Linsley et al., "Immunospression in Vivo by a Soluble Form of the CTLA–4 T Cell Activation Molecules", *Science*, vol. 257, pp. 792–795, (1992).

Linsley et al., "The Role of the CD28 Receptor During T Cell Responses to Antigen", *Annu. Rev. Immunol.*, vol. 11, pp. 191–212, (1993).

Linsley et al., "CE28 Engagement by B7/BB–1 Induced Transient Down–Regulation of CD28 Synthesis and Prolonged Unresponsiveness to CD28 Signaling", *The Journal of Immunology*, vol. 150, No. 8,; pp. 3161–3169, (1993).

Olson et al., "Concepts and Progress in the Development of Peptide Mimetics", *Journal of Medicinal Chemistry*, vol. 36, No. 21, pp. 3039–3049, (1993).

Peach et al., "Complementarity Determining Region 1 (CDR1)– and CDR3–analogous Regions in CTLA–4 and CD28 Determine the Binding to B7–1", *J. Exp. Med.*, vol. 180, pp. 2049–2058, (1994).

Peach et al., "Both Extracellular Immunoglobin–like Domains of CD80 Contains Residues Critical for Binding T Cell Surface Receptors CTLA–4 and CD28", *The Journal of Biological Chemistry*, vol. 270, No. 36, pp. 21181–21187, (1995).

Perrin et al., "Role of B7: CD28/CTLA–4 in the Introduction of Chronic Relapsing Experimental Allergic Encephalomyelitis", *J. Immunol.*, vol.. 154, pp. 1481–1490, (1995).

Sayegh et al., "CD28–B7 Blockade after Alloantigenic Challenge In Vivo Inhibits Th1 Cytokines but Spares Th2", *J. Exp. Med.*, vol. 181, pp. 1869–1874, (1995).

Steurer et al., "Ex Vivo Coating of Inlet Cell Allografts with Murine CTLA4/Fc Promotes Graft Tolerance", *J. Immunol.*, vol. 155, No. 3, pp. 1165–1174, (1995).

Turka et al., "T–cell activation by the CD28 ligand B7 is required for cardiac allograft rejection in vivo", *Proc. Natl. Acad.*, vol. 89, pp. 11102–11105, (1992).

Wallace et al., "CTLA4Ig Treatment Ameliorates the Lethality of Murine Graft–Versus–Host Disease Across Major Histocompatibility Complex Barriers", *Transplantation*, vol. 58, pp. 602–610, No. 5, (1994).

Wallace et al., "Induction and Reversal of Long–Lived Specific Unresponsiveness to a T–Dependent Antigen Following CTLA4Ig Treatment", *J. Immunol.*, vol. 154, pp. 5885–5889, (1995).

Harper et al., "CTLA–4, and CD28 Activated Lymphocyte Molecules are Closely Related in Both Mouse and Human as to Sequence, Message Expression, Gene Structure, and Chromosomal Location," *J. Immunol.*, Aug. 1991, vol. 147, pp. 1037–1044.

* cited by examiner

Co-Stimulatory Signal

Alignment of the REI Ig Homodimer with CD28/CTLA-4

```
 21  ILVKQSPMLVAYDNAV..NLSQKYSYNLFSREFRASLHKGLDSAV.EVCVV  CD28
  1  MHVAQPAVVLASSRGI.ASFVCEYASPGKATEVRVTVLRQADSQVTEVCAA  CTLA
  2  IQMTQSPSSLSASVGDRVTITQASQD.IIKYLNWYQQTPGKAPKLLIYEA  REI

69  YGNYSQQLQVYSKTGFNCDGKLGNESVTFYLQNFYVNQTDIYFCKIEVMY  CD28
 51  TYMMGNELTFLDDS...ICTGTSSGNQVNLTIQGLYICKVELMY  CTLA
 52  SNLQAG......VPS..RFSGSGSGTDYTFTISSQPEDIATYYQ..QQYQ  REI

119  PPPYLDNEKSNG  CD28
 99  PPPYY.LGIGNG  CTLA
 95  PYTFGQGTKLQI  REI
```

FIGURE 2

CTLA-4 Homodimer

Sequence Alignment of B7-1 with a Heavy Chain Ig (MCO)

```
B7-1    VIHVTKEVKEVATLSCGHNVSVEELAQTRIYWQ--KE--
              |: :||: :||  :::: ::
MCO        SGPGLVKPSEALSLTC--TVSGDSINTILYYWSWIRQPP

--KKMV-LTMM--SGDMNIWPEYKNR-TI-FDITNNLSIVIL-ALRPSDEGTYECVVLKYE
         |: :: |  ||:   |: |:|||  :::|    |   ::::|:::||:  |:
        GKGLEWIGYIYYSGSTYGNPSLKSRVTISVNTSKNQFYSKLSSVTAADTAVYYCARVPLV

KDAFKREHLAEV-TLSVKAD--FPTPSISDFEIPTSNIRRIICSTSGGFPEP-HLSWLEN
        ::: |: :|:| :|:  ::|||   :|  | :: ::::: :| :|| ::|| |||   ::
        VNPWGQGTLVTVSSASTKGPSVFPLAPSS--KSTSGGTAALGCLVKDYFPQPVTVSW-NS

GEELNAINTTVSQDPETELYAVSSKLDFNMTT--NHSFMCLIKYGHLRVNQTFNWNTTKQ
        |:   :::::||  :  ::::|||||:::     :::::: ::   |  |: |:::
        GALTSGVHTFPAVLQSSGLYSLSSVVTVPSSSLGTQTYICNVN--HKPSNTKVD

US 6,337,316 B1

PHARMACEUTICAL COMPOSITIONS THEREOF, AND METHODS OF USING SAME

This application is a continuation of copending parent application No. PCT/US98/12312, filed Jun. 11, 1998, which claims priority from prior U.S. provisional appln. No. 60/049,470, filed Jun. 12, 1997 and which is hereby incorporated entirely by reference.

BACKGROUND OF THE INVENTION

1. Field of the Invention

The present invention relates to peptidomimetics, capable of inhibiting CD28 and/or CTLA-4 interaction with CD80 (B7-1) and CD86 (B7-2), and pharmaceutical composition thereof. It also relates to the use of the peptidomimetic for the preparation of pharmaceutical compositions active in pathologies requiring CD28 and/or CTLA-4 agonism or antagonism and method of treating such pathologies.

2. Description of the Background Art

The interaction of antigen Presented in the contex: of MHC class II to the T Cell Antigen Receptor Complex (TCR) provides the primary signal to the Helper T Cell to initiate clonal proliferation. Optimal T cell activation, however, requires a co-stimulatory signal in addition to the engagement of the TCR. Although several co-stimulatory molecules have been implicated in initiating the "second signal", it has become apparent that one of the major signals is provided by the interaction of CD28 with B7 molecules (CD80 and CD86) presented on the surface of the antigen presenting cell (see FIG. 1).

Cell surface CD28 is a 201 amino acid glycoprotein member of the Ig-superfamily of proteins (Aruffo and Seed., 1987). It is found naturally as a homodimer and expressed constitutively on the surface of 80% of human T cells (all $CD4^+$ cells and on about 50% of the $CD8^+$ cells) and on virtually all murine T cells (Linsley and Ledbetter, 1993) Engagement of CD28 by its natural ligand B7-1 or B7-2 (CD80, CD86) results in a second signal to the T cell and an increase of IL-2 production along with down-regulation of the CD28 with respect to mRNA levels and cell surface expression (Linsley et al., 1993). The second signal is believed to be crucial for the commitment of antigen specific T cell to proliferate. Interference with this second signal in the presence of the first signal (TCR signal) results in antigen specific T cell anergy (unresponsiveness) (Linsley et al., 1992). During the period that CD28 is down-modulated, a closely related glycoprotein, CTLA-4, is concomitantly up-regulated (Freeman et al., 1992). It is generally thought that CD28 delivers the positive costimulatory signal for growth and differentiation, while CTLA-4 is responsible for a subsequent negative signal of the cellular activation events (for a review see Lenschow et al., 1996).

Both CD28 and CTLA-4 bind to the B7 family of proteins, most notably B7-2 and B7-1 (Azuma, et al., 1993). With regard to B7-1, it is known that CTLA-4Ig binds with a 20–100 fold higher affinity than CD28Ig (Linsley et al., 1991).

Freshly isolated human and murine B cells express low levels of B7-2 but not B7-1, however the levels of both 37's are up-regulated upon activation (Hathcock et al., 1994). In vitro studies have demonstrated that blockade of T cell co-stimulation via the CD28 signaling pathway results in the development of antigen-specific T cell anergy (Harding et al., 1991; Boussiotis et al., 1993; Linsley et al., 1991).

CTLA-4Ig has been used in a wide variety of animal models to study the in vivo efficacy of blocking the CD28 signaling pathway. The first in vivo studies showed that CTLA-4Ig was capable of suppressing humoral responses to a T cell dependent antigen (Linsley et al, 1992).

Other studies have demonstrated that locking the CD28 costimulatory signal is effective in preventing xenograft rejection (Lenschow et al., 1992), cardiac allograft rejection (Turka et al., 1992; Lin et al., 1993), murine systemic lupus (Finck et al, 1994; Chu et al., 1996), graft versus host disease (GVHD) (Wallace et al., 1995), and experimental allergic encephalomyelitis (EAE) (Cross et al., 1995; Perrin et al., 1995; Arima et al., 1996).

Administration of CTLA-4Ig at the time of allogeneic transplantation prolongs the graft survival but fails to prevent rejection (Turka et al., 1992). If one delays the administration of the CTLA-4Ig until 2 days after the transplant, then long-term survival of the allograft is observed as well as tolerance toward subsequent challenge with alloantigen in vivo (Lin et al., 1993; Sayegh et al., 1995).

Judge et al. (1996) recently studied the in vivo mechanism of action of CTLA-4Ig and found that delayed administration of the protein resulted in an 80–90% reduction in Th1-type cytokines and blunted the expansion of antigen specific T cells by 50%. Thus, CTLA-4Ig may be able to regulate the balance between Th1- and Th2-type responses.

In conclusion, there is ample evidence that blockade of the CD28 costimulatory pathway may be a useful therapeutic target for immune modulation. CTLA-4Ig is currently in Phase II clinical trials in psoriasis patients. However its practical use for chronic immunotherapy is limited by it being only parenterally administrable and recurring mg/kg doses.

A small molecule mimetic of CTLA-4/CD28 would have great clinical and commercial advantages and represents a long felt need.

Site-directed mutagenesis studies with both CTLA-4 and CD28 have implicated a hexapeptide stretch including several key sites in the CDR3 region of the protein, MetTyrProProProTyr (SEQ ID NO:31), as a critical contact site in the interaction with B7 (Peach et al., 1994).

European patent application EP 682,039 discloses that CTLA-4Ig fusion proteins block the interaction with B7 antigen. It also discloses CTLA-4 mutants, in which any of the amino acids, including the sequence MetTyrProProProTyr (SEQ ID NO:31), has been replaced by Ala.

International patent application WO 90/33770 is generally Directed to ligands for T cell surface molecules, especially CTLA-4, which induces antigen specific apoptosis of activated T cell. Isolated peptides containing CTLA-4 fragments, constituting the epitope for such binding, are also disclosed and claimed. Such epitopes include the amino acid sequence ProProTyrTyrLeu (SEQ ID NO:32) (partially overlapping with the above reported hexapeptide MetTyrProProProTyr (SEQ ID NO:31).

Scientists at Glaxo have recently attempted to use both linear as well as conformationally restrained peptides to mimic this region (Ellis et al., 1996). The Glaxo study, however, failed to yield any productive leads.

Citation of any document herein is not intended as an admission that such document is pertinent prior art, or considered material to the patentability of any claim of the present application. Any statement as to content or a date of any document is based on the information available to applicant at the time of filing and does no: constitute an admission as to the correctness of such a statement.

SUMMARY OF THE INVENTION

It is an object of the invention to overcome the deficiencies of the related art, such as noted above, by providing biologically active peptidomimetics of CD28 or CTLA-4.

Accordingly, the present invention provides for peptidomimetics of CD28 or CTLA-4 which are capable of inhibiting CD28 and/or CTLA-4 interaction with CD80 (B7-1) and CD86 (B7-2). The peptidomimetics of the present invention contain a core sequence corresponding to amino acid residues 2 to 9 of SEQ ID NO:1 and may be cyclized and may include additional amino acid residues N-terminal and/or C-terminal to this core sequence.

The present invention also provides for a pharmaceutical composition which includes the peptidomimetics according to the present invention, and pharmaceutically acceptable excipients.

Further provided in the present invention is a method of treating pathologies and disorders with are improved by inhibition of CD28 and/or CTLA-4 interaction with CD80 and CD86.

BRIEF DESCRIPTION OF THE DRAWINGS

FIG. 1 schematically illustrates the involvement of CD28 in Helper T cell Activation.

FIG. 2 shows the amino acid sequence alignment of CD28 (SEQ ID NO:33), CTLA-4 (SEQ ID NO:34), and REI (SEQ ID NO:35) used for the molecular modeling of CD28/CTLA-4.

FIG. 3 shows a molecular model in ribbon diagram form of the CTLA-4 homodimer based on the REI Template.

FIG. 4 shows the amino acid sequence alignment of the B7-1 protein (SEQ ID NO:36) with an IgG heavy chain of the MCO antibody (SEQ ID NO:37).

FIG. 5 shows a ribbon diagram of a CTLA-4 Monomer/B7-1 protein complex.

FIG. 6 shows a bar graph of an evaluation of AT 199, 200 and 201 peptides in a Human MLR(A vs B).

FIG. 7 shows a bar graph of an evaluation of AT 199, 200 and 201 peptides in a Human MLR (B vs A).

FIG. 8 shows a bar graph of an evaluation of AT 199 cyclized and linear peptides in a Human MLR (A vs B).

FIG. 9 shows a bar graph of an evaluation of AT 199 and 201 peptides in a murine MLR.

FIG. 10 shows a bar graph of a toxicity test of AT 199 and 200 peptides in THP-1, Jurkat and PBLs cells.

FIG. 11 shows a bar graph of the effect of AT 199 and 200 peptides on PHA-mediated stimulation of PBL.

DETAILED DESCRIPTION OF THE INVENTION

The biologically active peptidomimetics of CD28 or CTLA-4 according to the present invention have been designed using a molecular modeling strategy, based on a "skin and bones" type design, as discussed below.

Both CD28 and CTLA-4 proteins are homodimeric Ig superfamily members consisting of a single Ig variable domain. A homology search of the Brookhaven database of known structures was conducted and a crystallized example of an Ig homodimer (code—REI) was found. The sequence alignment used in the modeling studies is shown in FIG. 2.

The models of both CTLA-4 and CD28 were constructed using side chain replacements of the REI template. Because the length of the CDR3 loop in REI is two amino acids shorter than the corresponding region on either the CD28 or CTLA-4, a CDR3 loop of appropriate length (obtained from the Brookhaven database, PDB1JHL.ENT) was grafted on to the template molecule. The newly constructed model was minimized to convergence using a conjugate-gradient function. Five cycles of annealed dynamics (iterations of an energy-dependent simulation of molecular motion followed by an energetic minimization) were used to optimize the structure prior to a final minimization step. A ribbon diagram of the CTLA-4 homodimer is shown in FIG. 3.

The molecular model of the B7-1 molecule was constructed in an analogous fashion to the strategy used for CD28/CTLA-4. The best alignment found from a search of the Brookhaven database was the Ig heavy chain variable and constant domain or the MCO antibody. The sequence alignment used in building the B7-1 model is shown in FIG. 4.

After the model of B7-1 was constructed, a tentative model of the CTLA-4 (CD28)/B7-1 complex was built. Several groups have published extensive site-directed mutagenesis studies that were aimed at defining the CTLA-4/B7 surfaces involved in complex formation (Peach et al., 1994, 1995; Guo et al., 1995). These mutations were aligned on the modeled proteins and used as a guide in forming the homodimeric binding complex. For simplicity, FIG. 5 shows only the monomeric CTLA-4 molecule interacting with B7-1.

In the engineering of the peptidomimetics of CD28 or CTLA-4 as inhibitors of the CD28 costimulatory pathway, the molecular models described above were used as design templates. The peptidomimetics according to the present invention, which are capable of inhibiting CD28 and/or CTLA-4 interaction with CD80 (B7-1) and CD86 (B7-2) molecules have a core amino acid sequence, LeuMetTyrProProProTyrTyr, corresponding to amino acid residues 2 to 9 of SEQ ID NO:1. In addition to this core amino acid sequence, the peptidomimetic may have additional amino acid residues N-terminal to and/or C-terminal to amino acid residues 2 to 9 of SEQ ID NO:1.

Preferably, there is a Cys residue both immediately N-terminal and immediately C-terminal to the core amino acid sequence, as shown by SEQ ID NO:1. It is also preferrable that the petpidomimetic of the present invention be cyclized. When the cyclized peptidomimetics of the present invention includes the sequence of SEQ ID NO:1, the cyclization of the peptide preferably occurs via a Cys-Cys disulfide bridge between residue 1 (Cys) and 10 (Cys) of SEQ ID NO:1. Otherwise, the peptidomimetic can be cyclized with a linker, such as a synthetic chemical linker, that bridges residue 2 (Leu) and residue 9 (Tyr) of the core amino acid sequence which corresponds to residues 2 to 9 of SEQ ID NO:1. Thus, cyclization preferably occurs within one amino acid of residue 2 and residue 9 of SEQ ID NO:1. Other examples of synthetic chemical linkers include, but are not limited to, a Lys-Asp salt bridge, lanthanide cyclization, N-terminal to C-terminal cyclization, those chemical linkers disclosed in Olson et al. (1993), etc.

It is also preferred in the peptidomimetics of the present invention that up to eleven additional amino acid residues are present N-terminal to, and/or up to eleven additional amino acids are present C terminal to the core sequence corresponding to residues 2 to 9 of SEQ ID NO:1. More preferably, there are two additional amino acid residues both N-terminal and C-terminal to the sequence or SEQ ID NO:1, wherein these additional amino acid residues are positively charged amino acid residues. The amino acid sequence of SEQ ID NO:2 is an example of a preferred embodiment of a cyclized peptidomimetic of the present invention where cyclization occurs via a Cys-Cys disulfide bridge between residues 3 and 12 of SEQ ID NO:2.

The peptidomimetics according to the present invention may further include one or more of the amino acid sequences selected from SEQ ID NO:5, SEQ ID NO:7, SEQ ID NO:14; SEQ ID NO:19, and SEQ ID NO:20, which can be linked to each other and/or co the sequence of SEQ ID NO:1 or the sequence corresponding to residues 2 to 9 of SEQ ID NO:1 either directly or through a suitable synthetic chemical linker. The peptidomimetics of the present invention is also intended to encompass those peptidomimetics in which one or more bioisoteric fragments, such as are commonly used in drug design, are present in combination with or in place of the additional amino acids N-terminal and/or C-terminal to the core amino acid sequence.

It is noteworthy that the peptidomimetics of the present invention are not fragments of CTLA-4/CD28 molecules, but have been specifically designed and subsequently selected from among a number of possibilities based on the results of the biological tests reported in the Examples section.

The strategy employed here was to identify and exploit the potential contact surfaces of the CD28/CTLA-4 proteins with B7 as well as to select a region of the CD28/CTLA-4 molecule responsible for mediating homodimer formation as a means of potentially disrupting the appropriate presentation of the homodimers.

Six regions of the modeled CD28/CTLA-4 molecules were identified as potential targets (see Table 1) for peptide design.

TABLE 1

Engineered Peptides studied

| Peptide | Description | Sequence | SEQ ID NO: |
|---|---|---|---|
| AT 119.1 | CD28 N-terminal region | KILVKQS | 3 |
| AT 120.1 | CD28 N-terminal region | KYLVKQS | 4 |
| AT 121.1 | AT119.1 with C-term. acid | KILVKQS-OH | 3 |
| AT 122.1 | AT120.1 with C-term. acid | KYLVKQS-OH | 4 |
| AT 125.1 | CTLA-4 N-terminal region | HVEQPA-OH | 5* |
| AT 136.1 | CTLA-4 N-terminal region | HVAQPA | 5 |
| AT 137.1 | CTLA-4 N-terminal region | HVEQPA | 6 |
| CDR1 Loop | | | |
| AT 106.1 | CD28 CDR-1 region | KCSYNLFSREFC | 7* |
| AT 107.1 | CD28 CDR-1 region | CKYSYNLFSREFC | 8 |
| AT 118.1 | CTLA-4 CDR-1 region | ECASPGKATEVC | 9 |
| AT 123.1 | CTLA-4 CDR-1 region | CEYASPGKATEVC | 10 |
| 40-45 Loop | | | |
| AT 108.1 | CD28 40-45 loop | CKGLDSAVEC | 11 |
| AT 116.1 | CD28 40-45 loop | LDSAVEV | 12 |
| AT 117.1 | AT116.1 with C-term. acid | LDSAVEV-OH | 12 |
| AT 124.1 | CTLA-4 40-45 loop | ADSQVTEV-OH | 13 |
| AT 127.1 | CTLA-4 40-45 loop | ADSQVTEV | 13 |
| AT 128.1 | CTLA-4 40-45 loop | CRQADSQVTEC | 14* |
| 60-65 Loop | | | |
| AT 115.1 | CD28 60-65 loop | CSKTGFNC | 15 |
| AT 197.1 | CTLA-4 60-65 loop | NECTFCDD | 16 |
| AT 131.1 | CTLA-4 60-65 loop | CDDSIC | 17 |
| 70-75 Loop | | | |
| AT 132.1 | CTLA-4 70-75 loop | CSSGNQVC | 18 |
| AT 133.1 | CTLA-4 70-75 loop | CSSPNQVC | 19* |
| AT 135.1 | CTLA-4 70-75 loop | CSPNQC | 20 |
| CDR3 MYPPPY | | | |
| AT 109.1 | CD28 CDR-3 region | CMYPPYLRGGKC | 21 |
| AT 110.1 | CD28 CDR-3 region | CMYPPPYGKC | 22 |
| AT 111.1 | CD28 CDR-3 region | CMYPPQYGKC | 23 |
| AT 112.1 | CD28 CDR-3 region | CMYPPPYKAKC | 24 |
| AT 113.1 | CD28 CDR-3 region | CKIEVMYPPPYC | 25 |
| AT 114.1 | CD28 CDR-3 region | CKIEVMYPPPYLC | 26 |
| AT 129.1 | CTLA-4 CDR-3 region | CMYPPPYYRGGKC | 27 |
| AT 130.1 | CTLA-4 CDR-3 region | CMYPPPYYKAKC | 28 |
| AT 199.1 | CTLA-4 CDR-3 region hybrid | RKCLMYPPPYYCHH | 2* |
| AT 200.1 | CTLA-4 CDR-3 region hybrid | RKCLAYPPPYYCHH | 29 |
| AT 201.1 | CTLA-4 CDR-3 region hybrid | RKCLGYPPPYYCHH | 30 |

*Note:
Peptides that have shown, at least, some biological activity in the MLR assay.

The first region corresponds to the amino terminus of the protein. This is an elongated (β-strand) stretch of amino acids and is not amenable to the introduction of conformational restraints. The amino terminus is predicted to lie directly below the CDR3 region and to form part of the B7 contact surface.

The second region corresponds to the CDR1 analogous portion of the protein. The CDR1 domain has been shown via site-directed mutagenesis studies to be involved in the binding to B7 (Peach et al., 1994). Because the CDR1 region does not form a tight β-turn, but rather forms a loosely formed loop, it is difficult to design conformationally restrained peptides that closely resemble this region. The strategy employed here was to give maximal flexibility to the restrained peptides designed from this region.

The third set of peptides was made to the loop region between residues 40–45 which represents one of the major contact sites predicted to hold together the homodimer. Because the functional CD28/CTLA-4 expressed on the cell surface is predominately in the form of a homodimer (some evidence exists that there may be some involvement of monomeric presentation to B7), the objective with these analogs was to disrupt the homodimer formation.

The fourth set of peptides was derived from the 60–65 loop (SEQ ID NOs:15, 16 and 17) which is not predicted to be a part of the B7 contact surface, but constitutes a major surface exposed loop. According to the present model of interaction, peptides designed from this region should not possess any biologic activity. If any of these analogs were to display inhibitory activity, then it is evidence that the present model interaction was incorrect.

The loop formed by residues 70–75 is predicted to be directly involved in the contact with B7. Three analogs were synthesized from this region (see Table 1, SEQ ID NO: 18, 19 and 20). AT 132 represents the restrained native sequence. Modeling of this analog suggested that the intended loop was not stably formed. AT 133 was designed to correct this instability by introducing a proline (a relatively rigid, turn promoting residue) to replace the highly flexible glycyl residue. AT 135 is a shorter analog of AT 133, which is intended to probe the contribution of residues that flank the central portion of the 70–75 loop.

Finally, the CDR3 analogous region oft CTLA-4/CD28 was exploited (SEQ ID NOs: 21–30). Single site-directed mutations in this region of CTLA-4Ig completely abrogate the binding to B7 (Peach et al., 1994). Analog design from this region, however, presented some formidable engineering problems. The central hexapeptide sequence from this region is MetTyrProProProTyr (SEQ ID NO:31). These are relatively hydrophobic residues and the triple proline stretch is conformationally rigid. In terms of the molecular model of the CTLA-4/B7 complex, this region is predicted to be part of a deep contact. Experience has indicated that the most effective inhibitors of protein-protein interactions tend to require an electrostatically active "guide" sequence which mimics part of the initial "handshake" of the binding event. Consequently, a variety of different approaches were used in the engineering of the CDR3 panel of analogs. Analysis of the surface area around the CDR3 region of the protein indicated that it is surrounded by a positively charged potential. Therefore, lysine, arginine and histidine were incorporated toward the ends of the analogs to mimic this positive potential and to aid in the solubility properties of the synthesized peptide.

In the specific instance of AT 199, a hybrid analog was designed. Several different strategies were incorporated in to the design of this analog First, four highly charged (positive) residues were incorporated adjacent to the cysteines flanking both the amino and carboxy termini of the analog. Since hydrophobic residues tend to move away from hydrophilic residues, this design was also intended to partition the MetTyrProProProTyr (SEQ ID NO:31) loop away from the positively charged residues and help force the correct formation of the CDR3 turn. The flanking residues were selected to mimic residues that are spatially juxtaposed to the CDR3 region in the native protein and are involved in the binding to B7. They also represent important sites of electrostatic contact. The arginine at the amino terminus of the analog is a mimic of Arg33 in the native protein. The histidine residue at the carboxy terminus of the peptide is intended to mimic His2 at the amino terminus of the protein which lies directly below the CDR3 region.

Peptides AT 200 and AT 201 were designed as controls for AT 199. Previously, Peach at el. (1994) have shown that a single substitution of the methionine residue to an alanine residue in the CDR3 region results in complete abrogation or the binding of CTLA-4Ig to B7. Therefore, AT 200 is identical in sequence to AT 199, with the exception that Met is replaced by an Ala residue. AT 201 is also identical in sequence to AT 199, with the exception that Met is replaced by a flexible Gly residue.

The peptidomimetics of the present invention may be prepared by any well known procedure in the art, in particular, by the well established chemical synthesis procedures utilizing automated solid-phase peptide synthesizers followed by chromatographic purification. More particularly, the procedures disclosed in the Examples section may be followed for the preparation and preferably the cyclization of such peptides.

The pharmaceutical composition for treating pathologies and disorders which are improved by inhibition of CD28 and/or CTLA-4 interaction with CD80 and CD86 according to the present invention contains a substantially purified peptidomimetic as an active ingredient. Depending on whether the peptidomimetic includes one or more of the amino acid sequences of SEQ ID NO:5, SEQ ID NO:7, SEQ ID NO:14, SEQ ID NO:19, and SEQ ID NO:20, the pharmaceutical composition according to the present invention may further include one or more separate peptides having an amino acid sequence selected from SEQ ID NO:5, SEQ ID NO:7, SEQ ID NO:14, SEQ ID NO:19, and SEQ ID NO:20 which are not already present in the peptidomimetic.

Examples of pathologies and disorders in which the peptidomimetics according to the present invention can be advantageously used as a prophylactic, a therapeutic or a diagnostic are immune system diseases and cancer. Specific non-limiting examples include autoimmune diseases, such as psoriasis, multiple sclerosis, lupus erythematosus, diabetes, rheumatoid arthritis, and therapy for transplant rejection including solid organ and cellular transplants.

Further objects and advantages of the invention will be evident in the following description.

An embodiment of the invention is the administration of a pharmacologically active amount of the peptide of the invention to subjects at risk of developing pathologies and disorders which are improved by inhibition of CD28 and/or CTLA-4 interaction with CD80 and CD86 or to subjects already showing such pathologies and disorders.

Any route of administration compatible with the active principle can be used, but particularly preferred is the parenteral administration because systemic effects can be achieved in a short period of time. Parenteral administration may be by a number of different routes including, but no limited to, subcutaneous, intravenous, intradermal, intramuscular, intraperitoneal, intracerebral, intranasal, oral, transdermal, or buccal routes.

It is understood that the dosage o peptide to be administered will be dependent upon the age, sex, health, weight, kind of concurrent treatment, and frequency of treatment. The dosage will be tailored to an individual patient as is understood and determinable by one of skill is the art. The dosage can be between 0.1 and 20 mg/Kg body weight, and preferably between 0.1 and 1 mg/Kg body weight.

The pharmaceutical composition for parenteral use including the active principle and a suitable vehicle can be prepared in injectable form. Vehicles for the parenteral administration are well known in the art and include, for example, water, saline solution and physiologic buffers. The vehicle can contain smaller amounts of excipients in order to maintain the solution stability and isotonicity.

The preparation of the pharmaceutical compositions can be carried out according to the ordinary modalities, and preferably, the peptide content will be in the range between 10 mg/ml and 1,000 mg/ml.

The invention will now be described by means of the following examples and accompanying figures, which should not be construed as in any way limiting the present invention.

EXAMPLE 1

Peptide Synthesis 34 peptides were synthesized using standard Fmoc procedures as described below, where the abbreviations are as follows:

Acetonitrile (ACN), Benzyl (BZL), tert-Butyloxycarbonyl (BOC), Dichloromethane (DCM), Diisopropylethylamine (DIEA), Dimethyl Formamide(DMF), 5,5'-dithiobis [2-nitrobenzcic acid] (DTNB), 9-Fluorenylmechyloxycarbonyl (FMOC), 2-[1H-Benzotriazole-1-yl]-1,1,3,3-tetramethyluronium hexafluoro-phosphate (HBTU), 1-hydroxybenzotriazole (HOBt), N-methyl morpholine (NMM), N-methyl pyrrolidone (NMP), 2,2,5,7,8-Pentamethyl-chroman-6-sulfonyl (PMC), tert-Butyl (tBu), Triphenylmethyl (TRT), Trifluoroacetic acid (TFA), Hepta-fluorobutaric acid (HFBA).

Resins

The primary resin used is a Rink Amide Methylbenzylhydrilamine resin, which is a standard support for synthesizing peptides with a C-terminal amide. For peptides needing a C-terminal free carboxylic acid ending, Wang resins with the first Fmoc amino acid attached are used. The Wang resins, which contain a p-benzyloxybenzyl handle, are the standard supports for the preparation of peptide acids by the Fmoc solid phase batch synthesis strategy. Both types of resins were purchased from NovaBiochem.

| Amino Acids used in Synthesis | |
|---|---|
| Fmoc Amino Acids | Protecting Group |
| Ser, Thr, Asp, Glu | tBu |
| Cys, Asn, Gln, His | Trt |
| Arg | PMC |
| Lys | BOC |
| Trp | BOC |
| Ala, Gly, Ile, Met, Leu, Pro, Phe, Val | None |

Chain Assembly

Protected peptide chains are initially assembled using FMOC strategy on an Applied Biosystem, Inc. Model 431A Peptide Synthesizer or a Rainin Symphony Multiple Peptide Synthesizer. Both synthesizers utilize base-labile FMOC N-terminal protected amino acids with appropriate side chain protection groups, 20% piperidine for N-terminal deprotection and HBTU for amino acid activation and coupling.

Cleavage/Extraction

The standard cleavage cocktails used for removing side chain protecting groups and releasing the peptide from the resin: Mixture A: 95% TFA, 5% Deionized Water.

For peptides without arginine, methionine, tryptophan or amino acids with the trityl protecting group (cysteine, histidine, asparagine, glutamine) : Mixture B: 82.5% TFA, 5% phenol, 5% D.I. water, 5% thioanisole, 2.5% ethanedithiol.

For peptides containing arginine or methionine: Mixture B': 87% TFA, 4.3% D.I. water, 4.3% thioanisole, 4.3% ethanedithiol.

An alternative cocktail for peptides with arginines or methionine: Mixture C: 95% TFA, 2.5% D.I. water, 2.5% ethanedithiol.

For peptides without arginine or methionine and containing tryptophan or the trityl protecting group: the cleavage reaction is performed by using 100 mg–1 g of peptide-resin placed into a 20 ml glass vessel and cooled an ice bath. The cleavage cocktail is prepared and also cooled in an ice bath, then added to the peptide-resin for a final volume of approx. 10 ml. The vessel is removed from the ice bath and allowed to warm to room temperature. The vessel is capped and the reaction mixture stirred at room temperature for 1.5 hours. After 1.5 hours, the solution is vacuum filtered through a medium-to-coarse porosity filter into approx. 30 ml of cold MTBE (methyl-t-butyl ether). The reaction vessel is washed with 1 ml TFA and filtered through the same filter funnel into the cold MTBE. The entire suspension is then transferred to a 50 ml centrifuge tube and centrifuged for approx. 10 minutes at 2000 rpm at room temperature. The supernatant is aspirated, the precipitate resuspended in 40 ml cold MTBE and centrifuged again. This step is repeated once more. The final supernatant is aspirated and the precipitate is treated with nitrogen to evaporate most of the remaining ether. The peptide is then dissolved in 20–30 ml of aqueous 1%–10% Acetic Acid, diluted to approx. 100–150 ml with deionized water, shell frozen, and lyophilized.

EXAMPLE 2

Cyclization

Peptides designed with two cysteines for disulfide bond cyclization are processed in one of these two ways. If the crude peptide is shown by analytical HPLC to be at least 65% pure without any significant secondary peaks (>20% of main product), the peptide is first cyclized, then purified. This comprises about 90% of the peptides produced at the facility. If the crude peptide has significant secondary deletion products, it is initially purified, then cyclized, and then re-purified.

The method of cyclization is disulfide bond formation by air oxidation. 25 mg–100 mg of crude peptide is first dissolved in deionized water at a ratio of 6–10 ml/mg peptide. While stirring, the pH of the solution is raised to approx. 8.3 with 1.0 M $NH_4HCO_3$ (pH 8.5). The solution is stirred overnight at room temperature, with sufficient stirring to create a vortex that reaches near the bottom or the vessel. The next day (approx. 18–24 hrs.), peptide cyclization is checked by analytical reverse-phase HPLC for characteristic changes in retention time and a 280 nm absorbance due to the disulfide bond. The solution is then lyophilized and scored or purified by direct loading onto a preparative reverse-phase HPLC column.

Purification

1. Reverse Phase Preparative HPLC

Note: peptides that tend to be more hydrophobic in nature are purified using HFBA instead of TFA to improve the chromatographic resolution of the final product.

Conditions: System—Waters Delta Prep 4000

Column—Vydac reverse-phase C18, 10 μm, 2.2×25 cm (Cat No. 218TP1022)

Buffers—A: Water/ 0.1%TFA B: Acetonitrile/0.1%TFA

Flow Rate—15 ml/minute

Detection—Waters 484 UV detector, 220 nm

Gradient—Variable, usually 0.33% B/min up to 1.0% B/min

Lyophilized crude peptides are prepared by dissolving 50–100 mg of peptide in 200 ml of aqueous 0.1% TFA. Cyclized peptides already in solution a pH 8–8.5 are first quenched with neat TFA to lower the pH to the 2–3 range. The peptide solution is then loaded directly onto the preparative column through the "A" buffer reservoir line and the gradient program started. Collected fractions are run overnight on an autosampler analytical HPLC system, Overlapping fractions judged to be >95% pure by peak integration are pooled and lyophilized.

Sep-Pak Purification

Conditions: Equipment—Baker Solid Phase Extraction 12 port Manifold

Columns—Waters Vac 12 cc 2 gram Sep-Pak columns

Buffers—$H_2O$/0.1% TFA

20%, 30%, 50%, 99.9% Acetonitrile/0.1% TFA solutions

Crude lyophilized peptides are prepared by dissolving 15–25 mg peptide in 8 ml of aqueous 0.1% TFA. Sep-Pak columns are first conditioned with 30 ml 99.9% Acn/0.1% TFA, followed by 30 ml of $H_2O$/0.1%TFA. Peptide solutions are loaded, followed by another wash of $H_2O$/0.1%TFA, then eluted with either 20% or 30% Acn/0.1%TFA buffers. A final wash with 50% Acn/0.1%TFA is performed to ensure complete elution and for comparison. The load volume, $H_2O$ wash, 20%–30% Acn and 50% Acn volumes are collected separately and checked on analytical HPLC. Eluted peptide solutions are then diluted 3:1 with deionized $H_2O$ and lyophilized.

EXAMPLE 3

Characterization

1. Analytical Reverse-phase HPLC (For Check of Homogeneity of Final Product)

Conditions: System—Waters 500 pumps, 717 Autosampler, 490

Muitiwavelength UV Detector

Column—Vydac C 18,5 µm, 0.46×25 cm (Cat. No. 218TP54)

Buffers—A: H$_2$O/0.1% TFA B: ACN/ 0.1% TFA

Flow Rate—1 ml/minute

Detection—214 nm, 280 nm

Gradient—2% B/minute

Purified lyophilized peptide samples are prepared by dissolving 0.2–1.0 mg of peptide in aqueous 0.1% TFA to a concentration of 0.5–1.0 mg/ml. 15–18 µl are injected onto the column and eluted with a gradient program of 0–50% ACN in 25 minutes. Chromatogram data is collected and stored with the Waters Expert-ease software system.

2. Mass Spectrometry (For Checking Homogeneity and Covalent Structure)

System: Perceptive Biosystems Voyager Elite

Type: MALDI-TOF (Matrix assisted laser desorption/ionization Time-of-flight)

Matrix: alpha-Cyano 4-hydroxy cinnamic acid (Sigma, C-2020), 10 mg/ml in 67% ACN/0.1% TFA Peptide samples are prepared at 1–10 µmol conc. In 50% ACN/0.1% TFA. 0.5 µl of peptide sample, followed by 0.5 µl of matrix solution, is applied to analysis plate wells and allowed to dry. The analysis plate is loaded into the machine and the samples scanned and analyzed using a reflectron delayed-extraction method. For each sample, a cumulative data signal from 32–128 laser shots is collected and analyzed. Each run includes a sample well with a standard peptide for calibration.

3. Ellman's Reagent Test (To Check Disulfide Bond Cyclization)

Disulfide bond cyclization of peptides containing Tryptophan or Tyrosine cannot be checked by HPLC TV detection at 280 nm due to the high absorbance at that wavelength. The Ellman's reagent test for the presence of free sulphydryl groups of the Cysteine sidechain is an alternative indicator of disulfide bond formation.

Peptides are prepared at 0.5 mmol concentrations in reaction buffer (0.1 M sodium phosphate, pH 8). Ellman's reagent, DTNB, is prepared at a 4 mg/ml conc. and a standard of Cysteine hydrochloride monohydrate at a 0.5 mmol concentration in the same reaction buffer. 250 µl of sample, 50 µl of Ellman's reagent and 2.5 ml of reaction buffer are mixed and incubated at room temperature for 15 minutes. A blank sample of reaction buffer and a standard sample of cysteine is also tested. A yellow color indicates the presence of free sulphydryl groups.

EXAMPLE 4

Human Mixed Lymphocyte Response (MLR)

Isolation of PBLS

Whole blood from donors was obtained from Interstate Blood Bank, Memphis, Tenn. Blood specimens were handled in a biosafety level 2 containment facility as recommended for potentially infectious blood specimens in the CDC/NIH manual *Biosafety in Microbiological and Biomedical Laboratories;* 3rd edition, 1993, page 10. Peripheral blood mononuclear cells (PBMC) were separated from red blood cells and granulocytes by ficoll-hypaque purification. Whole peripheral blood was diluted 1:2 in PBS and 30 ml was overlayed onto 15 ml of ficoll-hypaque in 50 ml polypropylene tubes. The tubes were spun at 400×g for 30 min at 25° C. Following centrifugation, the interface between the upper plasma layer and the lower ficoll layer was collected, cells washed in RPMI-1640 2×, and viable counts determined using trypan blue. Cells to be used as responders in the assay were stored on ice until mitomycin C treatment of stimulator cells was completed.

Mitomycin C Treatment of Stimulators

PBMC, isolated as described above, to be used as stimulators in the assay were adjusted to 2–4×10$^6$ cells/ml in complete medium (RPMI 1640 containing 10% heat-inactivated human AB serum, 2 mM glutamine, 50 µM 2-mercaptoethanol and 100 U/ml penicillin-100 µg/ml streptomycin), and treated with mitomycin C (25 µg/ml) for 30 min in a 37° C. water bath. Following treatment, cells were washed with S volumes of complete medium 3×, and viable counts determine using trypan blue. To set up autologous stimulation controls some responder cells were also treated with mitomycin C as mentioned above.

CTLA-4Ig and Peptides

Purified CTLA-4Ig fusion protein was produced, as described in Steurer et al. 1995, from a NS-1 cell line kindly donated by Dr. T. Strom (Beth Israel Hospital, Boston, Mass.) as a 1 mg/ml solution in sterile PBS. The protein was stored frozen at −80° C. Upon thawing, the aliquot was stored at 4° C. Purified peptides were lyophilized according to known procedures. Peptides were reconstituted in sterile PBS, pH 7.4 at 2 mM concentration, aliquoted in microfuge cubes and stored frozen at −20° C. For the assay, an aliquot of the peptide was thawed and diluted to 200 µM in complete medium.

Mixed Lymphocyte Response Assay (Human)

For the one-way allogeneic mixed lymphocyte response (MLR) assay, responder cells were plated at 10$^6$ cells/well, and stimulator cells at 5×10$^4$ cells/well in 96-well round bottom plates. Cells were incubated with serial dilutions of the anti-CD4 Ab Leu 3A (1 µg/ml–0.06 µg/ml) in triplicate, or an isotype-matched control Ab. Cyclosporin A at 1 µg/ml was used as an additional control.

CTLA-4 Ig was serially diluted an.4 tested from 10 µg/ml to 0.15 µg/ml. Peptides were tested either directly or in the presence of a constant spiked-in dose of CTLA-4 Ig at 0.5 µg/ml. The plates were incubated at 37° C. in a humidified 5% CO$_2$ atmosphere for 7 days.

Proliferation of the cells was determined by pulsing the wells with $^3$H-Tdr (1 µCi/well) for the last 18 h of the assay. Plates were harvested using a Tomtec -late harvester and the counts incorporated determined using a Wallac microbeta-plate plus reader.

Mitogen Stimulation Assays

For these assays, ficoll-hypaque purified PBMC (10$^5$ cells/well) were incubated in flat-bottom 96-well tissue culture plates with indicated concentrations or phytohemagglutinin (PHA; 5, 2.5, 1.25, 0.5 µg/ml) for 3 days at 37° C. in a humidified 5% CO$_2$/air incubator. Cells were incubated in the presence or absence of various concentrations of CTLA-4 Ig, purified anti-CD80 mAb (1 µg/ml), anti-CD86 mAb (1 µg/ml), and peptides 199 and 201 serially diluted from 100 µM to 12.5 µM for the period of the assay.

Proliferation of the cells was determined by pulsing the wells with $^3$H-Tdr (1 µCi/well) for the last 6 h of the assay. Plates were harvested using a Tomtec plate harvester and the counts incorporated determined using a Wallac microbeta-plate plus reader.

EXAMPLE 5

Murine MLR

One-way murine MLRs were set up using the C57Bl/6 mice splenocytes as stimulators and BalB/c splenocytes as responders.

Isolation of Mouse Splenocytes

Spleens were excised from mice (Jackson Laboratories, Bar Harbor, Ma.) 6–8 weeks of age. Cells were separated from the capsule using sterile frosted glass slides and washed in cold RPMI 1640 1×. Red blood cells were lysed by treating the spleen cell suspension with cold Tris ammonium chloride buffer (2 ml/spleen) for 3 min on ice. After lysis, the cells were washed 2× in 5 volumes of complete medium (RPMI 1640 containing 10 % heat-inactivated FBS, 2 mM glutamine, 50 µM 2-mercaptoethanol, 100 U/ml penicillin-100 µg/ml strepcomycin, 1 mM sodium pyruvate and 1 mM non-essential amino acids).

Plastic-adherent cells were removed from splenocytes of BalB/c mice by adjusting the cell concentration to $3 \times 10^6$ cells/ml in complete medium and incubating the cells for 1.5–2 h at 37° C. in T-75 flasks. Following incubation non-adherent cells were collected by gently washing the flasks and the percent recovery determined (60–70%). Bal b/C responder cells were stored on ice until mitomycin C treatment of stimulator cells was completed.

Mitomycin C Treatment of Stimulators

Following RBC lysis splenocytes of C57Bl/6 mice were adjusted to $2-4 \times 10^6$ cells/ml in complete medium and treated with mitomycin C (50 µg/ml) for 30 min at 37° C. in a humidified 5% $CO_2$ in air atmosphere. Following treatment, cells were washed with 5 volumes of complete medium 3×, and viable counts determined using trypan blue.

To set up autologous stimulation controls some responder cells were also treated with mitomycin C as mentioned above.

Mixed Lymphocyte Response Assay (Murine)

For the assay, responder and stimulator cells were plated at 105 cells/well in 96-well round bottom plates. Cells were incubated with serial dilutions of an anti-CD4 Ab (50 ng/ml–0.05 ng/ml) in triplicate, or an isotype-matched control Ab. Cyclosporine A at 1 µg/ml was used as an additional control. CD28/CTLA-4 peptides 199 and 201 were serially diluted and tested at a final concentration or 100 µM to 1.56 µM. CTLA-4 Ig serially diluted from 10 µg/ml was used as a positive control for inhibiting the MLR.

Appropriate scrambled peptide controls and matrix controls were included in every assay. The plates were incubated at 37° C. in a humidified 5% CO2 in air atmosphere for 4 days. Proliferation of the cells was determined by pulsing the wells with 3H-Tdr (1 µCi/well) For the last 6 h of the assay. Plates were harvested and the counts incorporated determined as described above.

EXAMPLE 6

Biological Screening of the Peptides in the Human MLR and CTLA-4Ig Binding Assay A total of 34 peptides were tested for inhibition of lymphocyte proliferation in the human MLR. Each peptide was tested in a MLR at doses ranging from 12.5 to 100 µM. The activity of each peptide was identified by assigning a + and − tone peptide depending on its ability to inhibit lymphocyte proliferation in the MLR (cpms).

A − was assigned if all concentrations of peptide tested gave <15% change in cpm.

A +, ++, or +++ was assigned depending on the 30 degree of inhibition caused by the peptide, where:

+ was assigned when the concentration of peptide tested gave >20% change in cpm;

++ was assigned if the peptide tested gave >25% change in cpm in a dose dependant fashion; and +++ was assigned if the peptide tested gave >50% change in cpm in a dose dependent fashion. In addition to the MLR, these 34 peptides were also evaluated in a CTLA-4Ig/B7 binding assay in which the ability of these peptides to affect the binding of CTLA-4Ig to B7 on Cess B cells was examined by FACS analysis.

As with the MLR, a + or − was assigned to each peptide depending on its ability to effect CTLA-4Ig binding to Cess B cells; where − represents no change in binding, + represents a minor change of <10% in binding, and a ++ represents a change of >20% in binding. The results of the MLR and B7 binding analysis are shown in Table 3.

TABLE 3

Overview of MLR/Binding Data with the Peptide Panel

| Peptide Number | Human MLR 1/24, 1/31, 3/6, 4/17, 5/2 | Binding Assay 3/24, 3/25, 4/5, 4/25 |
|---|---|---|
| AT 106.1 | ++, +, +, +/− | ++, ++ |
| AT 107.1 | −, +, +, − | +/− |
| AT 108.1 | −, −, − | − |
| AT 109.1 | +/− | −, + |
| AT 110.1 | − | −, − |
| AT 111.1 | −, +/− | − |
| AT 112.1 | − | −, − |
| AT 113.1 | − | −, − |
| AT 114.1 | Toxic | Toxic |
| AT 115.1 | − | − |
| AT 116.1 | − | − |
| AT 117.1 | − | + |
| AT 118.1 | − | Not tested |
| AT 119.1 | −, +/− | − |
| AT 120.1 | −, +/− | − |
| AT 121.1 | +/−, − | +/− |
| AT 122.1 | −, − | +, − |
| AT 123.1 | −, − | +/−, − |
| AT 124.1 | −, − | +, − |
| AT 125.1 | −, − | −, + |
| AT 127.1 | −, − | +/−, +/− |
| AT 128.1 | ++, − | + |
| AT 129.1 | −, − | ++ |
| AT 130.1 | −, − | −, − |
| AT 131.1 | +, −, − | +/− |
| AT 132.1 | +, −, − | +, − |
| AT 133.1 | ++, + | ++, − |
| AT 134.1 | | |
| AT 135.1 | +/−, − | ++ |
| AT 136.1 | ++, +, − | +++, + |
| AT 137.1 | −, + | +/−, − |
| AT 197.1 | −, −, − | −, −, − |
| AT 199.1 | +, +, + | +, +, + |
| AT 200.1 | −, −, − | −, −, − |
| AT 201.1 | −, −, − | −, −, − |

The data from each peptide was analyzed without bias, such that the results from prior assays were not considered in determining whether a peptide was assigned a + or a −.

As can be seen from the table above, only a small number of peptides exhibited activity in either of these assays. Those peptides that exhibited activity in either the MLR or the binding assay (AT#s:106, 107, 128, 131, 132, 133, 135, 136, 199) were retested several times to determine if the initial observation was reproducible.

Based on the cumulative results of this analysis, peptides which exhibited semi-reproducible inhibition in either the MLR or the binding assay, or both., were selected for further analysis. The selected peptides were AT 106, 128, 133, 135, and 136, and later, peptide AT 199.

Analysis of Positive Peptides from Primary Screening (AT 106, 128, 133, 135, and 136)

Since peptides AT 106, 128, 133, 135, and 136 showed some activity in the MLR and/or binding assays during primary screening, these peptides were selected for further analysis. These peptides were retested in the MLR and binding assay either alone or in combination. In two MLRs, none of these peptide by themselves had any consistent effect on the MLR at concentrations up to 200 µM. Analysis of these same peptides in the Cess B binding assay showed no effect on CTLA-4Ig binding.

Identification and Evaluation of AT 199

Figure 6:
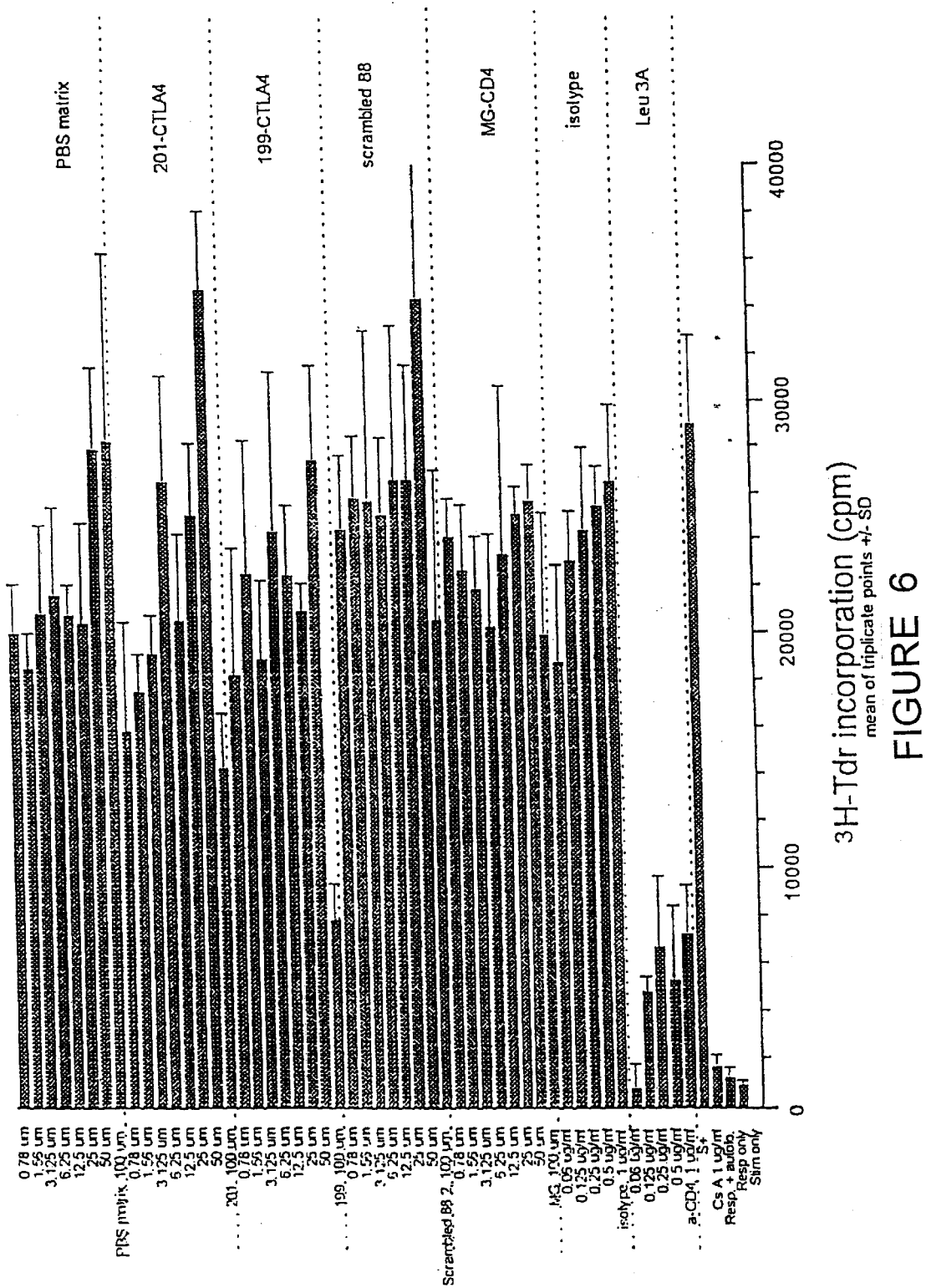
Figure 7:
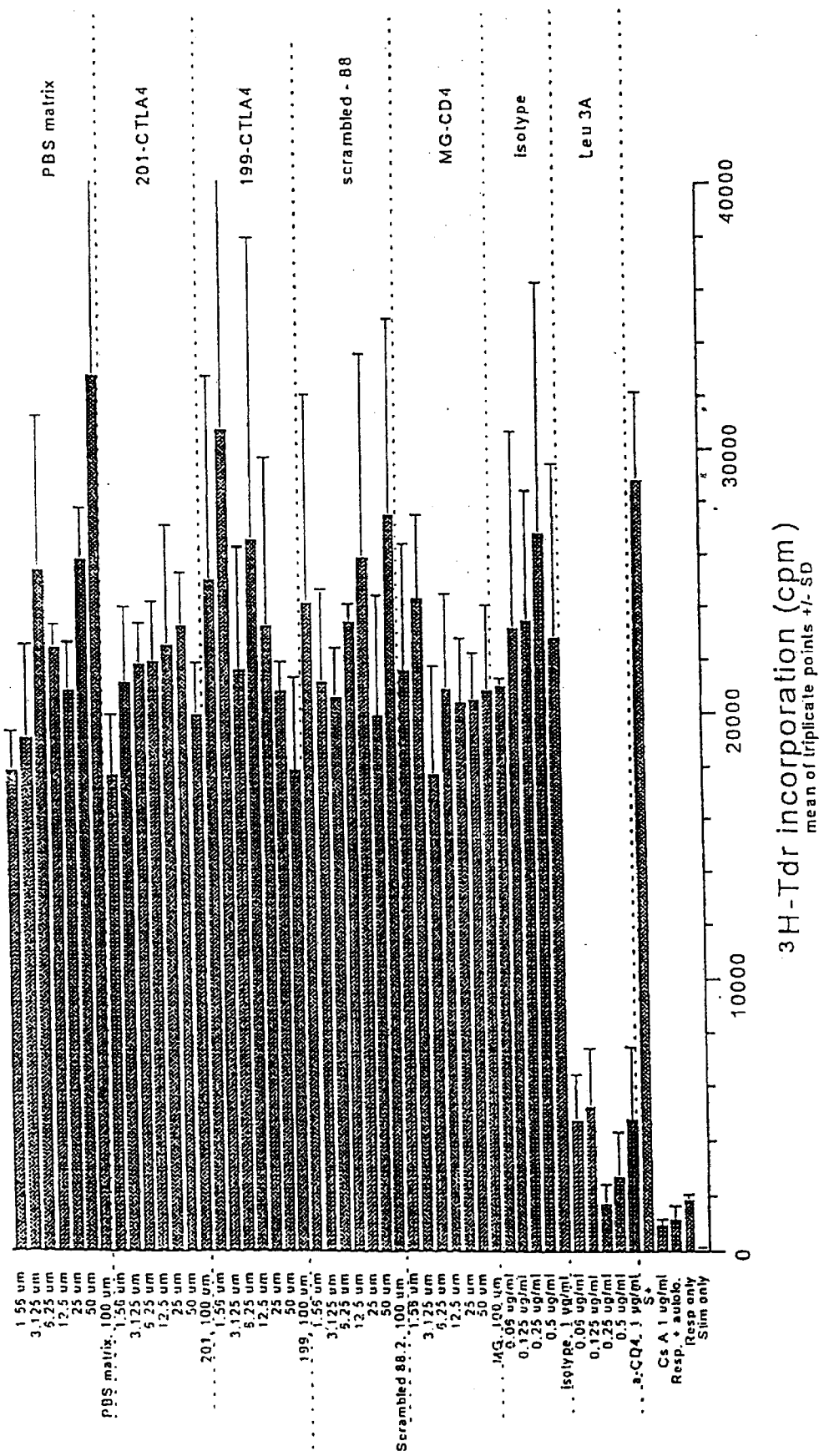

During the course of our screening effort, the last 3 peptides tested were peptides 199, 200, and 201. The results of two human MLRs comparing the activity of AT 199, 200, and 201 in the dose range of up to 100 µM are shown in FIGS. 6 and 7.

As can be seen in one MLR AT 199 inhibited lymphocyte proliferation by ~70% whereas in the other MLR it inhibited ~30%. The degree of lymphocyte proliferation (30,000 cpm) was the same in both assays. Though we have no explanation for the lower inhibition of AT 199 in this MLR, similar trends have been observed for CTLA-4Ig and may be a function of the state of the cells used to generate the MLR. That AT 199 did not inhibit both MLRs as effectively is suggestive of this peptide not being cytotoxic and that the activity of AT 199 is biologically significant. AT 199 was tested in a total of 6 human MLR assay and was active in 5 out of 6.

The mass spectrometer analyses of each of these analogs showed that the expected mass was obtained, however, AT 199 contained a significant portion of linear product (32%).

In order to show that the observe activity of AT 199 was not due to an artifact of synthesis and to distinguish whether the refolded analog or the free linear form of the analog is responsible for the inhibitory behavior seen in the MLR, three new batches of AT 199 were produced.

AT 199.2A was a resynthesis of AT 199.1, where the refolding conditions were prolonged to 5 days and the pH of the refolding buffer raised from pH 8.5 to pH 10.0 to aid in the efficiency of the procedure.

AT 199.2B was treated with iodoacetamide in order to purify a purely linear analog. This procedure modifies the free sulphydryls through a simple alkylation of the sulfurs such that the cysteines are not sterically hindered but are also neither reactive nor available for forming a disulfide bridge.

AT 199.3 was a resynthesis of AT 199.1 using the original protocols without change. Table 4 shows a summary of the AT 199 analogs synthesized and the results of a quantitative Ellman's reaction to ascertain the balance between covalently cyclized and free linear populations.

TABLE 4

Results of the free sulphydryl content of the AT 199 Analogs

| Peptide | % Cyclized vs. Linear |
|---|---|
| AT 199.1 | 68% cycl.: 32% lin. |
| AT 199.2A | 94.1% cycl.: 5.9% lin. |
| AT 199.2B | 0% cycl.: 100% lin. |
| AT 199.3 | 98.4% cycl.: 1.6% lin. |

The newly synthesized batches of AT 199 were used to more specifically address whether linear or cyclized populations of AT 199 are responsible for the activity seen with this analog (note—it is unclear why the AT 199.3 cyclized more efficiently than AT 199.1, since identical procedures were used). The population of free sulphydryl-containing linear peptide was reduced by more than an order of magnitude in the AT 199.3 analog relative to the original batch. If the activity observed in the previous MLR's were due to free linear analogs, then one would expect to see a dramatic reduction in activity in the AT 199.3. The inhibitory profile associated with the alkylated AT 199.2B should be able to tell us whether or not the observed activity is related to conformational specificity.

Evaluation of AT 199.3, 199.2A and 199.2B in the Human MLR

As described above, another synthesis of AT 199 was conducted (199.3) along with the generation of a linear (199.2B) and a fully cyclized (199.2A) version of AT 199. These peptides were evaluated in different human MLRs in comparison co peptide AT 201 and in the presence and absence of CTLA-4Ig (0.5 µg/ml).

AT 199.3 and 199.2A inhibited the MLR 30% and 50%, respectively, at 100 µM in one MLR, and by 700 and 25%, respectively, in another MLR. AT 199.2B, on the other hand, inhibited <10% in the MLR's at the highest concentration (100 µM) tested. From this result we conclude that AT 199 requires a cyclized conformation to be active.

Figure 8:
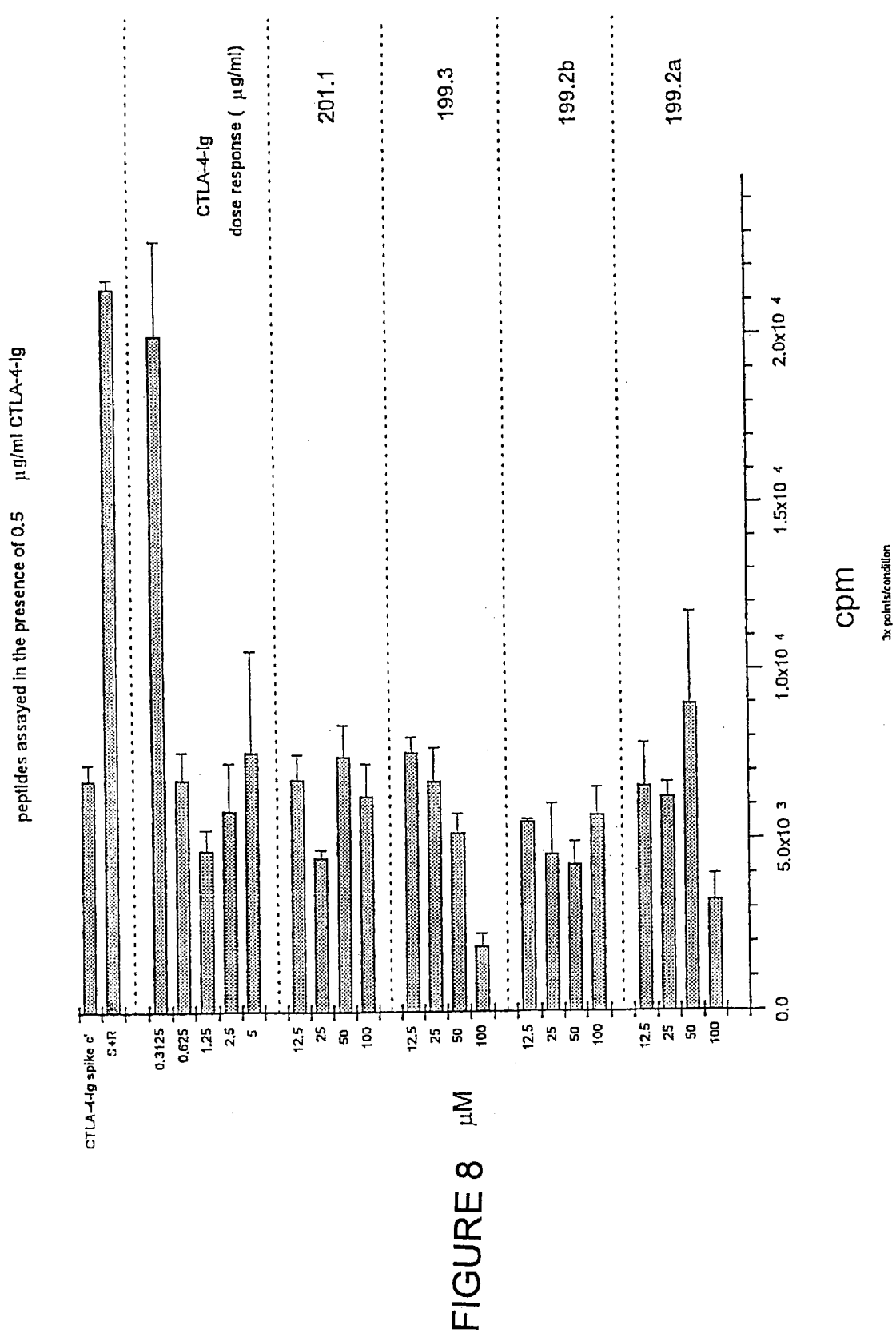

These peptides were also tested for activity in other 2 MLRs in which CTLA-4Ig was spiked in at 0.5 µg/ml. The results of one of these studies are shown in FIG. 8.

At 199.3, when added with 0.5 µg/ml of CTLA-4Ig, inhibited the MLR over and above CTLA-4Ig by itself. AT 199.2A also was additive when added in combination with CTLA-4Ig, but A 199.2B and peptide 201 had no effect when added in combination with CTLA-4Ig. These results suggest that the cyclized AT 199 has activity at inhibiting the human MLR and can enhance the effect of CTLA-4Ig.

Evaluation of AT 199 in a Murine MLR

Figure 9:
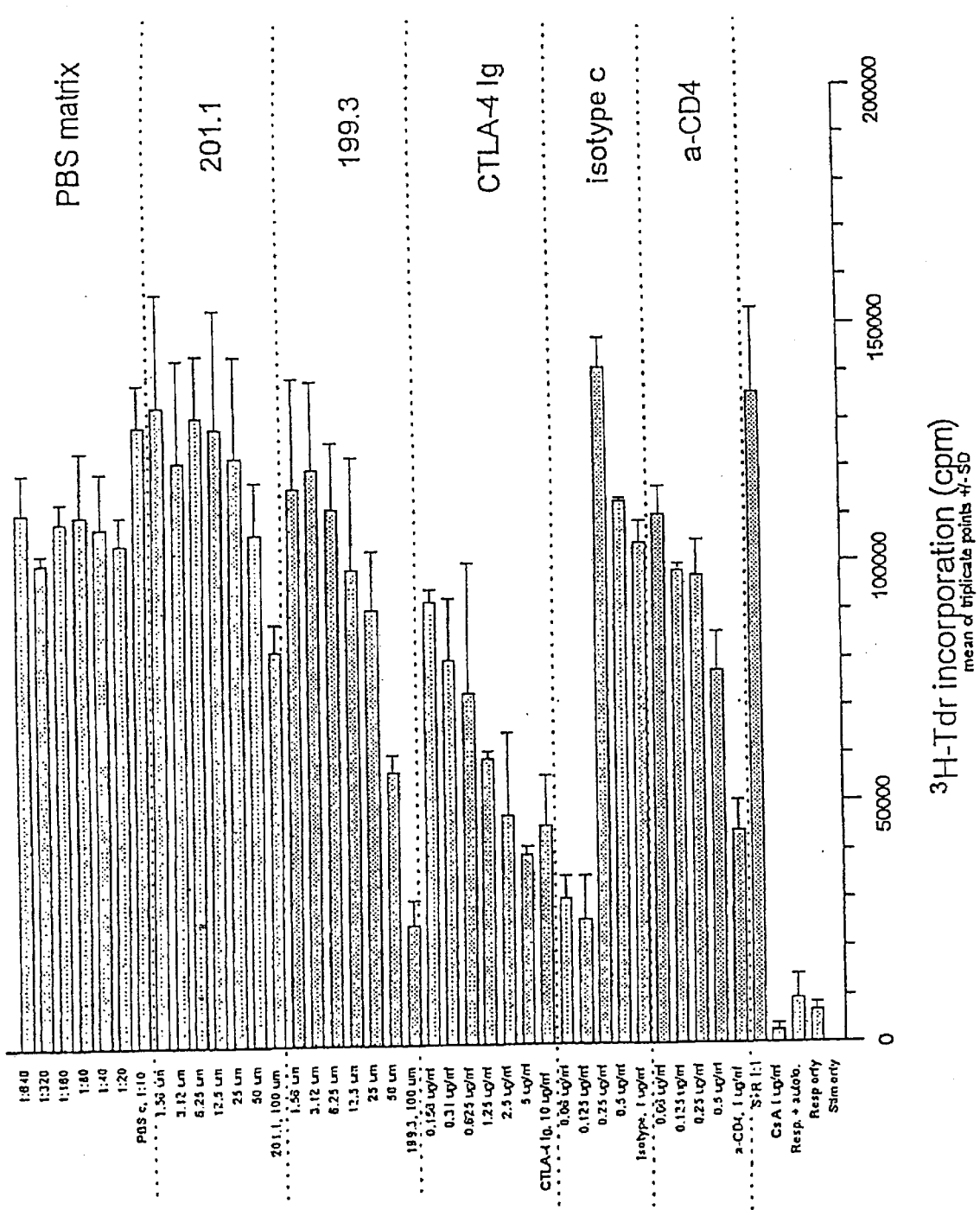

The primary sequence of CTLA-4 is very similar between human and mouse. A murine CTLA-4Ig was used throughout these studies to inhibit a human MLR. Therefore, activity of AT 199 was tested on a murine MLR. The results of this study are shown in FIG. 9.

AT 199.3 inhibited the murine MLR 85% which was similar to the inhibition by 10 µg/ml of CTLA-4Ig itself. Peptide 201 in this same assay inhibited only 25%. Thus, it appears that like CTLA-4Ig, AT 199 is active in both the human and mouse system.

Toxicity Evaluation of AT 199 and 201 Peptides

To determine if the activity of AT 199 was due to a specific effect on lymphocyte proliferation in the MLR or due to a non-specific inhibition of lymphocyte proliferation in general (i.e., toxicity), the toxicity of AT 199 was tested against THP-1, Jurkat, and resting and activated PBLs. The results of these experiments are shown in FIG. 10.

Figure 10:
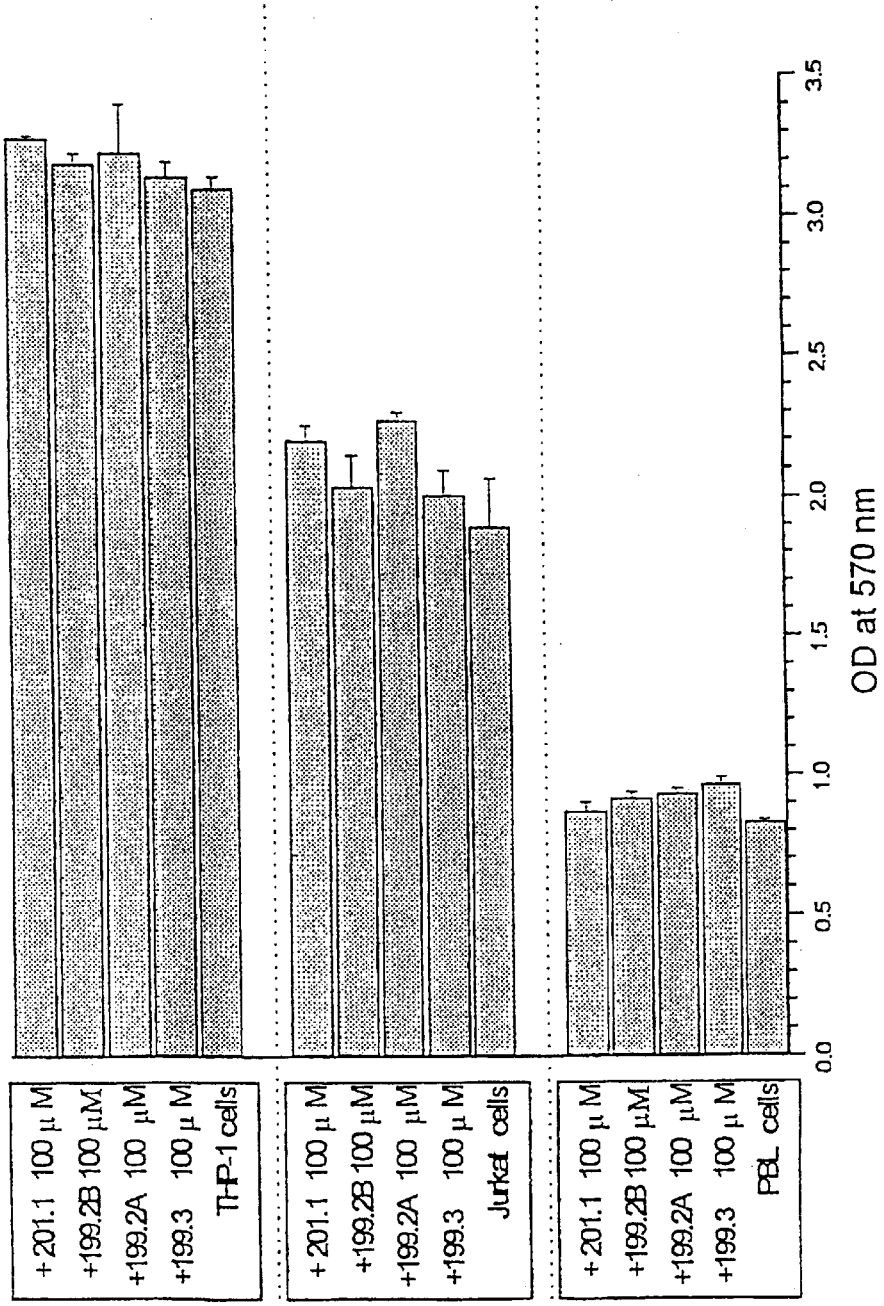

As seen in FIG. 10, no inhibition of THP-1, Jurkat or resting primary PBLs was observed in the presence of 100 µM AT 199.

AT 199 was tested for inhibition of PHA activated PBLs. PHA activation, while not specifically targeted at the CD28 pathway, has some dependence on this pathway depending on the concentration of PHA used to activate lymphocytes. To determine the AT 199 of phytohemagglutinin (PHA) activation on CD28 signaling, CTLA-4Ig was included in each assay.

Figure 11:
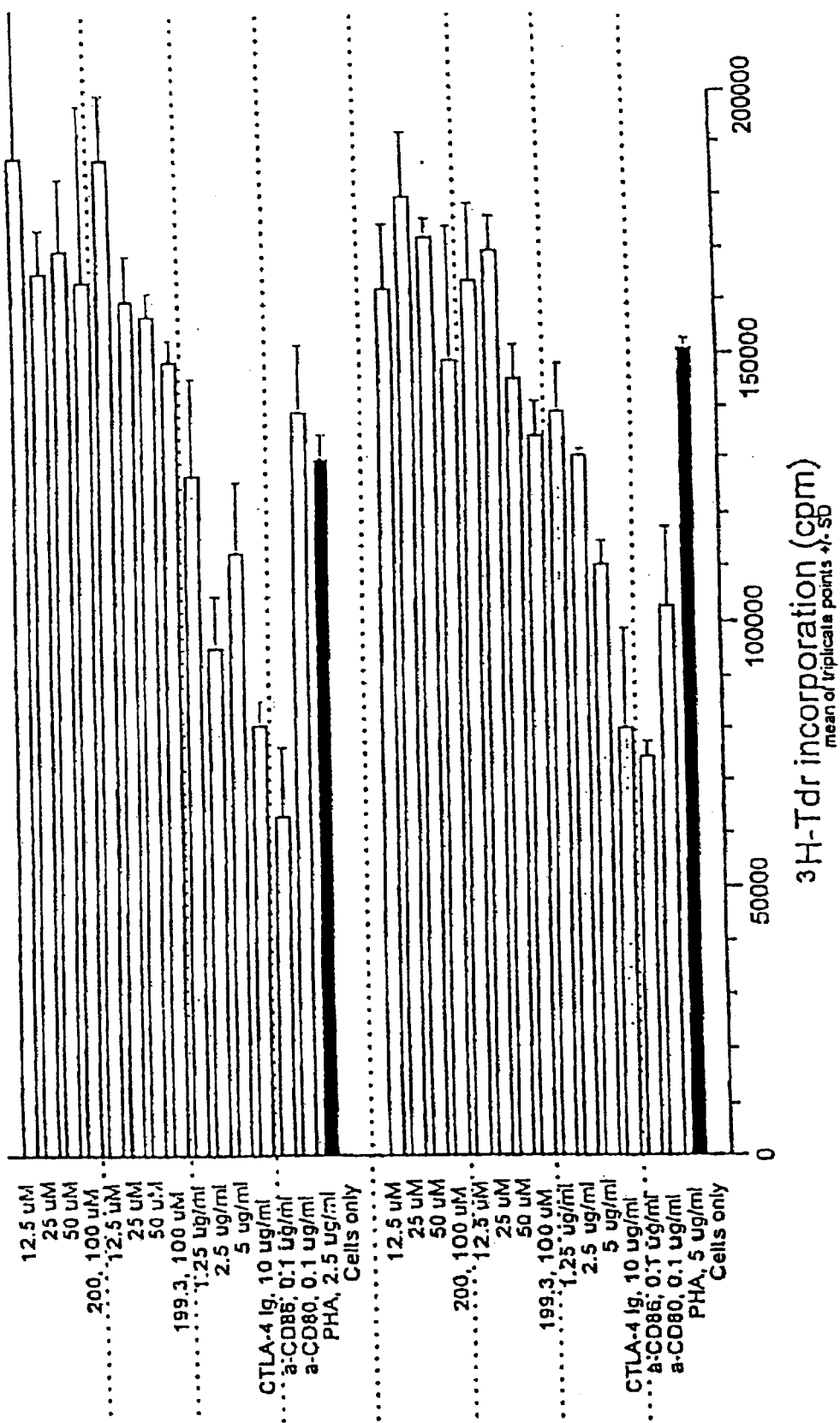

The effect of AT 199 on a representative PHA activation is shown in FIG. 11. As can be seen in FIG. 11, 10 µg/ml CTLA-4Ig inhibited PHA activation by ~40–50% at both concentrations of PHA (2.5 and 5 µg/ml). AT 199 on the other hand had only a minor effect on inhibiting PHA activation in this experiment suggesting that PHA activation of lymphocytes from this particular donor was only partially working through the CD28 pathway. Thus, AT 199 is not toxic to lymphocytes, but appears to have lower potency than CTLA-4Ig to act on the B7/B28 pathway.

AT 199, derived from the CDR3 domain, was the only peptide of the 34 analogs assayed that exhibited significant, reproducible inhibition in the MLR by itself. The inhibition was dose dependent and exhibited an apparent $IC_{50}$ between 50–100 µM. Peach et al. (1994) have shown that a single Met to Ala substitution in the CDR3 region of human CTLA-4 abolishes the ability of the protein to bind to B7. Based on this observation, two control peptides of AT 199 were synthesized in which the Met was changed to either Ala (AT 200) or Gly (AT 201). Other than these single amino acid changes, the control peptides were identical to AT 199. These control peptides did not inhibit any of the MLRs as much as AT 199 in which they were assayed. Thus, AT 199 appears to exhibit sequence specificity in its ability to inhibit the MLR.

AT 199 was treated with iodoacetamide in order to alkylate the sulfurs on the peptide such that a disulfide bridge could not form. This linear peptide, AT 199.2B, had no effect on the proliferation of the MLR. Thus, AT 199 appears to possess conformational specificity.

AT 199 and its control analogs were assayed for overt toxicity and non-specific inhibition. The peptides were added to growing cultures of THP-1 cells, Jurkat cells and primary peripheral blood lymphocytes (PBLs). No effect was observed on the growth of any of these cell cultures indicating that the inhibition observed in the MLR was not due to toxicity.

In order to test for an unanticipated mechanism of inhibition, AT 199 was assayed using PHA-stimulation of PBLs. Phytohemagglutinin (PHA) is a lectin extracted from the red kidney bean and is a mixture of five tetrameric glycoprotein. PHA stimulates T cells in the presence of accessory cells (but not B cells) by cross-linking a variety of critical T cell surface molecules, including CD3, CD2, CD4, CD8 and LFA-1 (Geppert, 1992). The involvement of CD28 in this stimulation is dependent on the degree of crosslinking by PHA. At the appropriate concentration of PHA, the simultaneous engagement of cell surface receptors results in a proliferation response that can bypass the need for specific costimulatory signals such as CD28. This can be monitored by examining CTLA-4Ig inhibition of PHA mitogenesis. AT 199 did not inhibit the PHA stimulated T cells under the same conditions in which the MLR was dramatically inhibited CTLA-4Ig inhibited PHA activation slightly. Thus, this data is consistent with a biologic effect directed at a specific aspect of T cell activation.

From the data reported here using 34 peptides, it can be concluded that at least 1 peptide (AT 199) which alone inhibits a CD28 dependent human immune response has been isolated.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may se applied to the essential features hereinbefore set forth as fallows in the scope of the appended aims.

All references cited herein, including journal articles or abstracts, published or unpublished U.S. or foreign patent applications, issued U.S. or foreign patents, or any ocher references, are entirely incorporated by reference herein, including all data, tables, figures, and text presented in the cited references. Additionally, the entire consents of the references cited within the references cited herein are also entirely incorporated by, reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents or the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Arima, T. et al., Inhibition by CTLA-4Ig of experimental allergic encephalomyelitis. *J. Immunol.* 156: 4916–4924 (1996).

Aruffo, A. et al., Molecular cloning of a CD28 cDNA by high-efficiency COS cell expression system. *Proc. Natl. Acad. Sci. USA* 84:8573–8577 (1987).

Azuma, M. et al., B70 antigen is a second ligand for CTLA-4 and CD28. *Nature* 366:76–79 (1993).

Boussiotis, V. A. et al., B7 but not intracellular adhesion molecule-1 constimulation prevents the induction of human alloantigen-specific tolerance. *J. Exp. Med.* 178: 1753–1759 (1993).

Chu, G. B. et al., Intervention of CD4+ cell subset shifts and autoimmunity in the BXSB mouse by murine CTLA-4Ig. *J. Immunol.* 156:1262–1268 (1996).

Cross, A. H. et al., Long-term inhibition of murine experimental autoimmune encephalomyelitis using CTLA-4-Fc supports a key role for CD28 costimulation. *J. Clin. Invest.* 95:2783–2789 (1995).

Ellis, J. H. et al., Interactions of CD80 and CD86 with CD28 and CTLA-4. *J. Immunol.* 56:2700–2709 (1996).

Finck, B. K. et al., Treatment of murine lupus with CTLA-4Ig. *Science* 265:1225–1228 (1994).

Freeman, G. J. et al., CTLA-4 and CD28 mRNA are coexpressed in most T cells after activation. Expression of CTLA-4 and CD28 mRNA does not correlate with the pattern of lymphokine production. *J. Immunol.* 149:3795–3801 (1992).

Geppert, T. "Phytohemaglutinin" in *Encyclopedia of Immunology*, (eds) Roitt, I M and Delves, P J. Academic Press, London pp. 1233–1234.

Guo, Y. et al., Mutational analysis and an alternatively spliced product of B7 defines its CD28/CTLA-4-binding site on immunoglobulin C-like domain. *J. Exp. Med.* 181:1345–1355 (1995).

Hathcock, K. S. et al., Comparative analysis of B7-1 and B7-2 costimulatory ligands: expression and function. *J. Exp. Med.* 180:631–640 (1994).

Harding, F. A. et al., CD28-mediated signalling co-stimulates murine T cells and prevents induction of anergy in C-cell clones. *Nature* 356:607–609 (1991).

Judge, T. A. et al., The in vivo mechanism of action of CTLA-4Ig. *J. Immunol.* 156: 2294–2299 (1996).

Lenschow, D. J. et al., Long-term survival of xenogeneic pancreatic islet grafts induced by CTLA-4Ig. *Science* 257:789–791 (1992).

Lenschow, D. J. et al., Differential effects of anti-B7-1 and anti-B7-2 monoclonal antibody treatment on the development of diabetes in the nonobese diabetic mouse. *J. Exp. Med.* 181:1145–1155 (1995).

Lenschow, D. J. et al., CD28/B7 system of T cell costimulation. *Ann. Rev. Immunol.* 14: 233–258 (1996).

Lin, H. et al., Long-term acceptance of major histocompatibility complex mismatched cardiac allografts induced by CTLA-4Ig plus donor-specific transfusion. *J. Exp. Med.* 178:1801–1807 (1993).

Linsley, P. S. et al., CTLA-4 is a second receptor for the B cell activation antigen B7. *J. Exp. Med.* 174:561–568 (1991).

Linsley, P. S. et al., Immunosuppression in vivo by a soluble form of the CTLA-4 T cell activation molecule. *Science* 257:792–794 (1992).

Linsley et al., The role of the CD28 receptor during T cell responses to antigen. *Ann. Rev. Immunol.* 11: 191–212 (1993).

Linsley, P. S. et al., CD28 engagement by B7/BB-1 induces transient down-regulation of CD28 synthesis and prolonged unresponsiveness to CD28 signaling. *J. Immunol.* 150:3161–3169 (1993).

Olson, G. L. et al., Concepts and progress in the development of peptide mimetics. *J. Medicinal Chem.* 36:3039–3049 (1993).

Peach, R. J. et al., Complementarity determining region 1 (CDR1)- and CDR3-analogous regions in CTLA-4 and CD28 determine the binding to B7-1. *J. Exp. Med.* 180:2049–2058 (1994).

Peach, R. J. et al., Both extracellular immunoglobulin-like domains of CD80 contain residues critical for binding T Cell surface receptors CTLA-4 and CD28. *J. Biol. Chem.* 270:21181–21187 (1995).

Perrin, P. J. et al., Role of B7:CD28/CTLA-4 in the induction or chronic relapsing experimental allergic encephalomyelitis. *J. Immunol.* 154:1481–1490 (1995).

Sayegh, M. H. et al., CD28-B7 blockade after alloantigenic challenge in vivo inhibits Th1 cytokines but spares Th2. *J Exp. Med.* 181:1869–1874 (1995).

Steurer, W. et al., Ex vivo coating of islte cell allografts with murine CTLA-4/Fc promotes graft tolerance. *J. Immunol.* 155 (3):1165–1174 (1995).

Turka, L. A. et al., T cell activation by the CD28-ligand B7 is required for cardiac allograft rejection in vivo. *Proc. Natl. Acad. Sci. USA* 89:11102–11106 (1992).

Wallace, P. M. et al., CTLA-4Ig treatment ameliorates the lethality of murine graft-versus-host disease across major histocompatibility complex barriers. *Transplantation* 58:602–608 (1994).

Wallace, P. M. et al., Induction and reversal of long-lived specific unresponsiveness to a T-dependent antigen following CTLA-4Ig treatment. *J. Immunol.* 154: 5885–5889 (1995).

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
Cys Leu Met Tyr Pro Pro Pro Tyr Tyr Cys
1               5                   10
```

(2) INFORMATION FOR SEQ ID NO: 2:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

```
Arg Lys Cys Leu Met Tyr Pro Pro Pro Tyr Tyr Cys His His
1               5                   10
```

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Lys Ile Leu Val Lys Gln Ser
1               5
```

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Lys Tyr Leu Val Lys Gln Ser
1               5
```

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
His Val Ala Gln Pro Ala
1               5
```

(2) INFORMATION FOR SEQ ID NO: 6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
His Val Glu Gln Pro Ala
1               5
```

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Lys Cys Ser Tyr Asn Leu Phe Ser Arg Glu Phe Cys
1               5                   10
```

(2) INFORMATION FOR SEQ ID NO: 8:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Cys Lys Tyr Ser Tyr Asn Leu Phe Ser Arg Glu Phe Cys
1               5                   10
```

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Glu Cys Ala Ser Pro Gly Lys Ala Thr Glu Val Cys
1               5                   10
```

(2) INFORMATION FOR SEQ ID NO: 10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Cys Glu Tyr Ala Ser Pro Gly Lys Ala Thr Glu Val Cys
1               5                   10
```

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Cys Lys Gly Leu Asp Ser Ala Val Glu Cys
1               5                   10
```

(2) INFORMATION FOR SEQ ID NO: 12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Leu Asp Ser Ala Val Glu Val
```

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Ala Asp Ser Gln Val Thr Glu Val
1               5
```

(2) INFORMATION FOR SEQ ID NO: 14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Cys Arg Gln Ala Asp Ser Gln Val Thr Glu Cys
1               5                   10
```

(2) INFORMATION FOR SEQ ID NO: 15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Cys Ser Lys Thr Gly Phe Asn Cys
1               5
```

(2) INFORMATION FOR SEQ ID NO: 16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Asn Glu Cys Thr Phe Cys Asp Asp
1               5
```

(2) INFORMATION FOR SEQ ID NO: 17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Cys Asp Asp Ser Ile Cys
1               5
```

(2) INFORMATION FOR SEQ ID NO: 18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Cys Ser Ser Gly Asn Gln Val Cys
1               5
```

(2) INFORMATION FOR SEQ ID NO: 19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Cys Ser Ser Pro Asn Gln Val Cys
1               5
```

(2) INFORMATION FOR SEQ ID NO: 20:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

```
Cys Ser Pro Asn Gln Cys
1               5
```

(2) INFORMATION FOR SEQ ID NO: 21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

```
Cys Met Tyr Pro Pro Tyr Leu Arg Gly Gly Lys Cys
1               5                   10
```

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Cys Met Tyr Pro Pro Tyr Gly Lys Cys
1               5                   10

(2) INFORMATION FOR SEQ ID NO: 23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Cys Met Tyr Pro Pro Gln Tyr Gly Lys Cys
1               5                   10

(2) INFORMATION FOR SEQ ID NO: 24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Cys Met Tyr Pro Pro Pro Tyr Lys Ala Lys Cys
1               5                   10

(2) INFORMATION FOR SEQ ID NO: 25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Cys Lys Ile Glu Val Met Tyr Pro Pro Pro Tyr Cys
1               5                   10

(2) INFORMATION FOR SEQ ID NO: 26:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Cys Lys Ile Glu Val Met Tyr Pro Pro Pro Tyr Leu Cys
1               5                   10

(2) INFORMATION FOR SEQ ID NO: 27:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide

```
       (xi) SEQUENCE DESCRIPTION: SEQ ID NO: 27:

Cys Met Tyr Pro Pro Tyr Tyr Arg Gly Gly Lys Cys
1               5                  10

(2) INFORMATION FOR SEQ ID NO: 28:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 28:

Cys Met Tyr Pro Pro Tyr Tyr Lys Ala Lys Cys
1               5                  10

(2) INFORMATION FOR SEQ ID NO: 29:

(i) SEQUENCE CHARACTERISTICS:
           (A) LENGTH: 14 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 29:

Arg Lys Cys Leu Ala Tyr Pro Pro Tyr Tyr Cys His His
1               5                  10

(2) INFORMATION FOR SEQ ID NO: 30:

(i) SEQUENCE CHARACTERISTICS:
           (A) LENGTH: 14 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 30:

Arg Lys Cys Leu Gly Tyr Pro Pro Tyr Tyr Cys His His
1               5                  10

(2) INFORMATION FOR SEQ ID NO: 31:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 31:

Met Tyr Pro Pro Pro Tyr
1               5

(2) INFORMATION FOR SEQ ID NO: 32:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide
```

(xi) SEQUENCE DESCRIPTION: SEQ ID NO: 32:

Pro Pro Tyr Tyr Leu
1               5

(2) INFORMATION FOR SEQ ID NO: 33:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Ile Leu Val Lys Gln Ser Pro Met Leu Val Ala Tyr Asp Asn Ala Val
1               5                   10                  15

Asn Leu Ser Cys Lys Tyr Ser Tyr Asn Leu Phe Ser Arg Glu Phe Arg
            20                  25                  30

Ala Ser Leu His Lys Gly Leu Asp Ser Ala Val Glu Val Cys Val Val
            35                  40                  45

Tyr Gly Asn Tyr Ser Gln Gln Leu Gln Val Tyr Ser Lys Thr Gly Phe
        50                  55                  60

Asn Cys Asp Gly Lys Leu Gly Asn Glu Ser Val Thr Phe Tyr Leu Gln
65                  70                  75                  80

Asn Leu Tyr Val Asn Gln Thr Asp Ile Tyr Phe Cys Lys Ile Glu Val
                85                  90                  95

Met Tyr Pro Pro Pro Tyr Leu Asp Asn Glu Lys Ser Asn Gly
            100                 105                 110

(2) INFORMATION FOR SEQ ID NO: 34:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
            50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly
            100                 105

(2) INFORMATION FOR SEQ ID NO: 35:

(i) SEQUENCE CHARACTERISTICS:
        (A) LENGTH: 103 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 35:

Ile Gln Met Thr Gln Ser Pro Ser Ser Leu Ser Ala Ser Val Gly Asp
1               5                   10                  15

Arg Val Thr Ile Thr Cys Gln Ala Ser Gln Asp Ile Ile Lys Tyr Leu
            20                  25                  30

Asn Trp Tyr Gln Gln Thr Pro Gly Lys Ala Pro Lys Leu Leu Ile Tyr
        35                  40                  45

Glu Ala Ser Asn Leu Gln Ala Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Tyr Gln Pro Tyr Thr Phe Gly
                85                  90                  95

Gln Gly Thr Lys Leu Gln Ile
            100

(2) INFORMATION FOR SEQ ID NO: 36:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
```

(2) INFORMATION FOR SEQ ID NO: 37:

(i) SEQUENCE CHARACTERISTICS:
        (A) LENGTH: 219 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Ser Gly Pro Gly Leu Val Lys Pro Ser Glu Ala Leu Ser Leu Thr Cys
 1               5                  10                  15
Thr Val Ser Gly Asp Ser Ile Asn Thr Ile Leu Tyr Tyr Trp Ser Trp
             20                  25                  30
Ile Arg Gln Pro Pro Gly Lys Gly Leu Glu Trp Ile Gly Tyr Ile Tyr
         35                  40                  45
Tyr Ser Gly Ser Thr Tyr Gly Asn Pro Ser Leu Lys Ser Arg Val Thr
     50                  55                  60
Ile Ser Val Asn Thr Ser Lys Asn Gln Phe Tyr Ser Lys Leu Ser Ser
 65                  70                  75                  80
Val Thr Ala Ala Asp Thr Ala Val Tyr Tyr Cys Ala Arg Val Pro Leu
                 85                  90                  95
Val Val Asn Pro Trp Gly Gln Gly Thr Leu Val Thr Val Ser Ser Ala
             100                 105                 110
Ser Thr Lys Gly Pro Ser Val Phe Pro Leu Ala Pro Ser Ser Lys Ser
         115                 120                 125
Thr Ser Gly Gly Thr Ala Ala Leu Gly Cys Leu Val Lys Asp Tyr Phe
     130                 135                 140
Pro Gln Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
                 165                 170                 175
Ser Ser Val Val Thr Val Pro Ser Ser Ser Leu Gly Thr Gln Thr Tyr
             180                 185                 190
Ile Cys Asn Val Asn His Lys Pro Ser Asn Thr Lys Val Asp Lys Arg
         195                 200                 205
Val Ala Pro Glu Leu Leu Gly Gly Pro Ser Val
     210                 215
```

What is claimed is:

1. A peptidomimetic compound comprising the amino acid sequence of SEQ ID NO:2, wherein said peptidomimetic compound is cyclized via a Cys-Cys disulfide bridge between amino acid residues 3 and 12 of SEQ ID NO:2.

2. A composition comprising the cyclized peptidomimetic compound according to claim 1, and a pharmaceutically acceptable excipient.

3. The composition according to claim 2, wherein said cyclized peptidomimetic compound further comprises a peptide having an amino acid sequence selected from the group consisting of SEQ ID NO:5, SEQ ID NO:7, SEQ ID NO:14, SEQ ID NO:19 and SEQ ID NO:20, or a combination thereof.

4. The peptidomimetic compound according to claim 1, wherein said peptidomimetic compound further comprises 1 to 10 positively charged N-terminal and C-terminal amino acid residues.

5. The peptidomimetic compound according to claim 4, wherein said positively charged amino acid residues are selected from the group consisting of lysine, arginine and histidine.

6. The peptidomimetic compound according to claim 1 which consists of the amino acid sequence of SEQ ID NO:2.

* * * * *